United States Patent [19]

Ikemoto et al.

[11] Patent Number: 5,164,113
[45] Date of Patent: * Nov. 17, 1992

[54] OPTICAL ACTIVE COMPOUND AND LIQUID CRYSTAL COMPOSITION

[75] Inventors: Tetsuya Ikemoto; Keiichi Sakashita; Seiji Hayashi; Yoshitaka Kageyama; Yoshihiro Sako, all of Kawasaki; Kenji Mori, Tokyo, all of Japan; Jun Nakauchi, New York, N.Y.

[73] Assignee: Mitsubishi Rayon Co., Ltd., Tokyo, Japan

[*] Notice: The portion of the term of this patent subsequent to Sep. 22, 2009 has been disclaimed.

[21] Appl. No.: 515,754

[22] Filed: Apr. 30, 1990

[30] Foreign Application Priority Data

May 2, 1989 [JP] Japan .................. 1-112935
May 19, 1989 [JP] Japan .................. 1-127482

[51] Int. Cl.$^5$ ...................... C09K 19/34; C09K 19/52
[52] U.S. Cl. .......................... 252/299.61; 252/299.01
[58] Field of Search ................. 252/299.01, 299.61

[56] References Cited

U.S. PATENT DOCUMENTS 4,576,732 3/1986 Isogai et al. .............. 252/299.65
4,818,431 4/1989 Eidenschink et al. ...... 252/299.61
4,871,472 10/1989 Kraun et al. .............. 252/299.65

FOREIGN PATENT DOCUMENTS 0117476 2/1984 European Pat. Off. .
0313379 10/1988 European Pat. Off. .

OTHER PUBLICATIONS

Jun Nakauchi et al., "Novel Ferroelectric Liquid Crystals With Very Large Spontaneous Polarization," Japanese Journal of Applied Physics, Jul. 28, 1989, No. 7, Part 2.

Primary Examiner—Robert L. Stoll
Assistant Examiner—C. Harris
Attorney, Agent, or Firm—Finnegan, Henderson, Farabow, Garrett & Dunner

[57] ABSTRACT

An optically active compound represented by the formula:

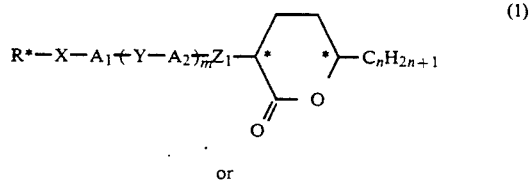

or

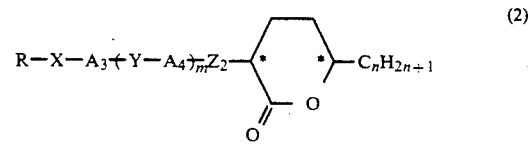

3 Claims, 3 Drawing Sheets

OPTICAL ACTIVE COMPOUND AND LIQUID CRYSTAL COMPOSITION

BACKGROUND OF THE INVENTION (1) This invention relates to a novel optical active compound and a liquid crystal composition comprising this optical active compound.

(2) Description of the Related Art

Liquid crystals currently used in a liquid crystal display (LCD) are classified into the nematic phase, and since they are of the light-receiving type, they are characterized in that there is no eye fatigue therefrom and the power consumption is very small. Nevertheless, these liquid crystals have problems in that the response speed is low and the view angle of the display is narrow.

Display devices and printer heads using a ferroelectric liquid crystal having advantageous characteristics similar to those of the nematic liquid crystal such as the property of not fatiguing eyes and the small power consumption and also having high response speed and high contrast characteristics comparable to those of a light-emitting type display element has been investigated.

The discovery of the ferroelectric liquid crystal were reported for the first time by R. B. Meyer et al [J. Physique, 36, L-69 (1975]. This ferroelectric liquid crystal is classified into the one exhibiting chiral smectic C phase (hereinafter referred to as "Sm*C phase"), and a typical instance of the ferroelectric liquid crystal is p-decyloxybenzylidene-p'-amino-2-methylbutyl cinnamate (hereinafter referred to as "DOBAMBC") represented by the following formula

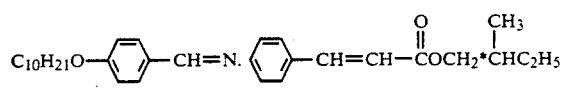

In DOBAMBC and most of the ferroelectric liquid crystals proposed hereafter, the range of temperatures showing the ferroelectric property (the range of temperatures where the Sm*C phase is present) is very narrow, and these liquid crystal materials cannot practically be used alone. Therefore, attempts have been made to expand the range of temperatures showing the Sm*C phase to the lower and higher temperature sides, taking room temperature as the center, by mixing a variety of ferroelectric liquid crystals. A ferroelectric liquid crystal having a larger spontaneous polarization than heretofore proposed ferroelectric liquid crystals is desired for a printer head for which a very short response time is required.

Nevertheless, in the case of mixtures of ferroelectric liquid crystals having an Sm*C phase, the kinds of compounds (liquid crystals) to be mixed are limited, and a liquid crystal mixture having satisfactory performances is difficult to obtain at the present. Moreover, a compound having a Schiff base, such as DOBAMBC, has a poor light stability and is readily colored.

SUMMARY OF THE INVENTION

Therefore, a primary object of the present invention is to provide a ferroelectric liquid crystal which is schematically stable, is not colored, has a good light stability, and a short response time, and a liquid crystal composition comprising this ferroelectric liquid crystal.

Another object of the present invention is to provide a compound which does not show a liquid crystal property, but has characteristics such that when the compound is incorporated in the ferroelectric liquid crystal composition, the compound exerts effects of increasing the spontaneous polarization of the liquid crystal composition and improving the response time, without degradation of the chemical stability and light stability, and thus preventing the coloration.

In accordance with the present invention, there is provided an optically active compound having a δ-valerolactone ring, which is represented by the following formula (1) or (2):

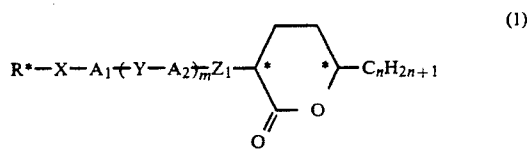

or

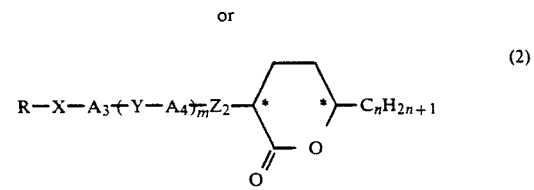

wherein R* represents $CH_3(CH_2)_q{}^*CH(CH_2)_p-$ in which p is an integer of from 0 to 11 and q is an integer of from 1 to 12, with the proviso that the sum of p and q is up to 12,

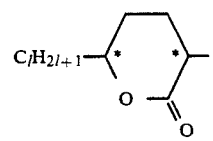

in which l is an integer of from 1 to 14, or

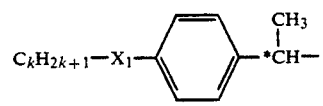

in which k is an integer of from 1 to 14 and $X_1$ is a direct bond or —O—, *C represents an asymmetric carbon atom, R represents a linear alkyl group having 1 to 18 carbon atoms, an optically active monohalogenalkyl group having 1 to 18 carbon atoms, or an optically active alkyl group having 1 to 18 carbon atoms with a methyl branch, X is a direct bond, —O—, —$CO_2$— or —OCO—, with the proviso that when R* is

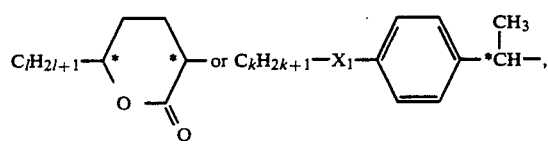

X is —O—, —OCO— or —$OCH_2$—, Y is a direct bond, —OCO—, —$CO_2$—, —$CH_2O$— or —$OCH_2$—, $A_1$ and $A_2$ represent one of A₃ and A₄ is

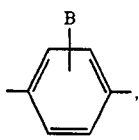, while the other of A₃ and A₄ represents

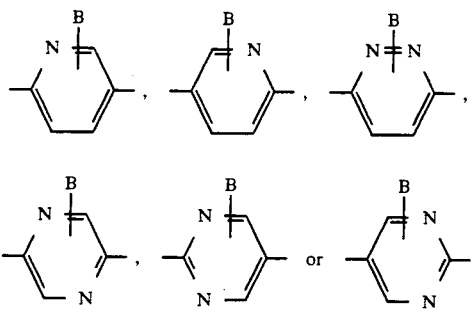

in which B represents a hydrogen atom, a halogen atom such as fluorine or chlorine, or a cyano group, m is 0 or 1, n is an integer of from 1 to 14, $Z_1$ is —$CO_2$—, —$CH_2O$— or —O—, and $Z_2$ is —$CO_2$—, —$CH_2O$— or —O—, with the proviso that when m is 0 in formula (2), A₃ is

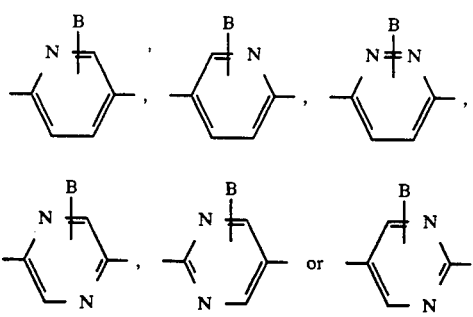

and when Y is a direct bond and $Z_2$ is —O— in formula (2), the combination of A₃ and A₄ is neither a combination of

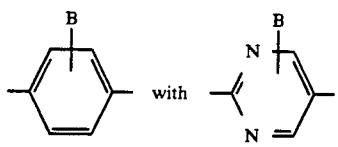

nor a combination of

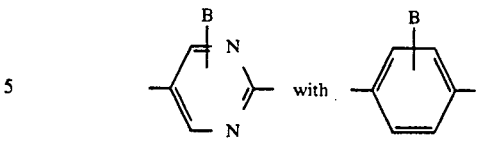

Furthermore, in accordance with present invention, there is provided a liquid crystal composition which comprises at least one member selected from the group consisting of compounds represented by the above-mentioned formula (1) and compounds represented by the above-mentioned formula (2).

DESCRIPTION OF THE PREFERRED EMBODIMENTS

Figure 1:
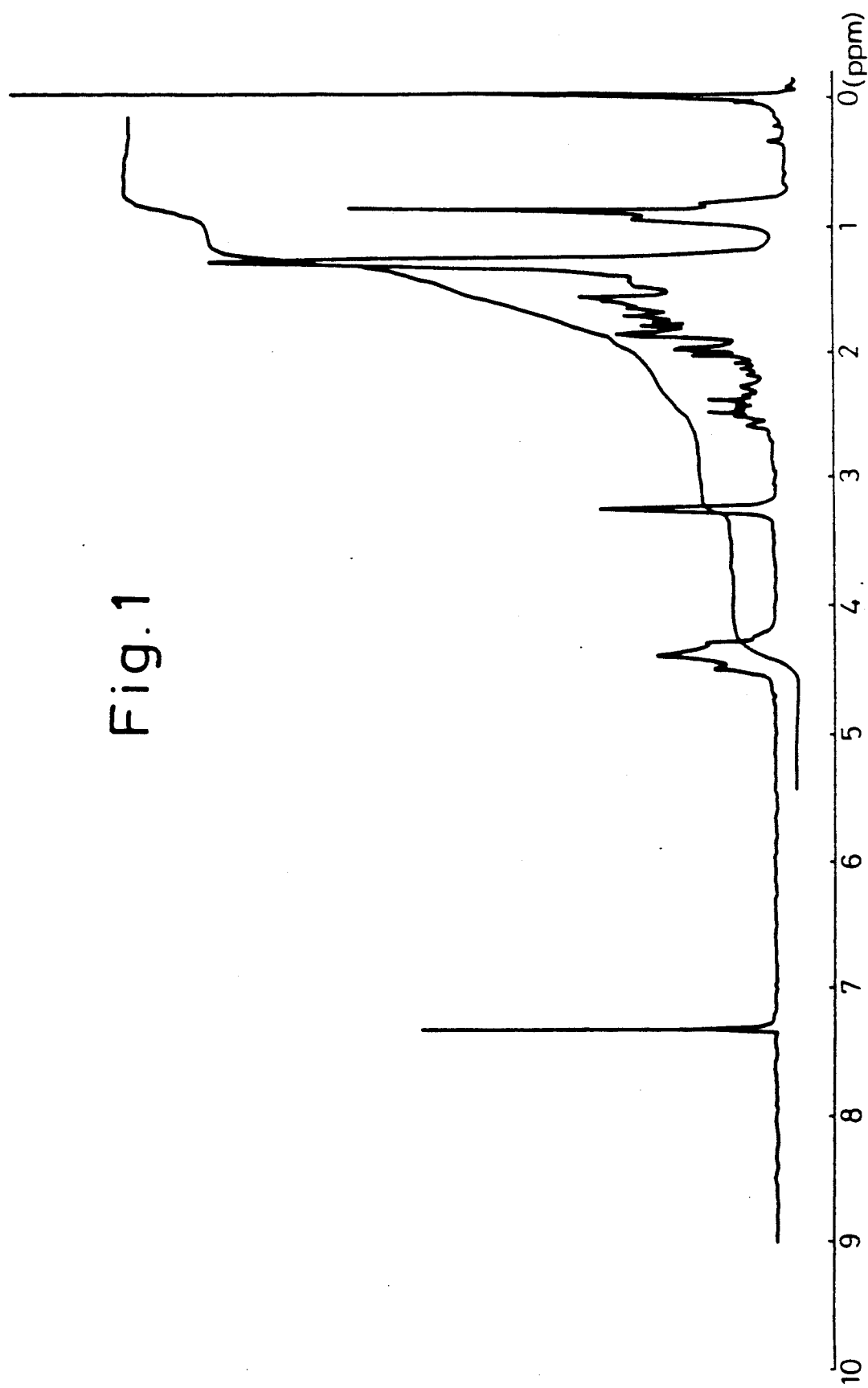
FIG. 1 shows the NMR spectrum of (2S,5RS)-2-hydroxy-5-hexyl-δ-valerolactone.

In the compound represented by formula (1), if n or l is 15 or larger, purification of the optically active lactone is relatively difficult, and if p is 12 or larger, the compatibility with other liquid crystals exhibiting the chiral smectic C phase (hereafter referred to as "Sm*C phase") tends to decrease. If q is 13 or larger, purification of a compound used as the intermediate, which is represented by the following formula:

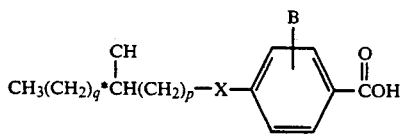

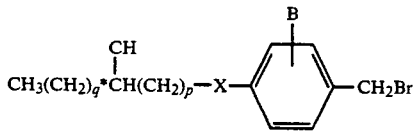

is difficult, and when the compound of formula (2) is mixed with other liquid crystal, the spontaneous polarization is often decreased.

In the compound represented by formula (2), R represents a linear alkyl group, an optically active monohalogenoalkyl group or an optically active alkyl group with a methyl branch. The number of carbon atoms included in the linear alkyl group is 1 to 18, preferably 4 to 14. If R is an optically active monohalogenoalkyl group or an optically active alkyl group with a methyl branch, R is preferably represented by the following formula:

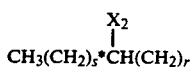

wherein $X_2$ is fluorine, bromine, chlorine or a methyl group, r is an integer of from 0 to 12, and s is an integer of from 0 to 12, with the proviso that the requirement of $2 \leq (r+s) \leq 12$ is satisfied.

As preferable examples of —A$_3$—Y—A$_4$)$_m$ in the compound of formula (2), there can be mentioned the following groups:
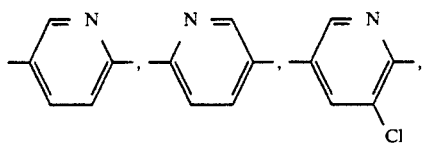
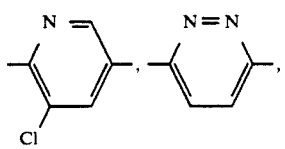
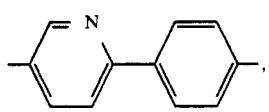
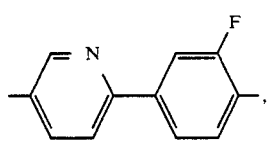
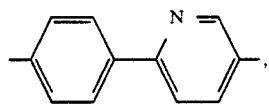
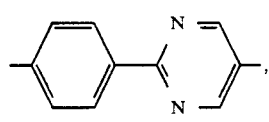
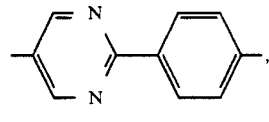
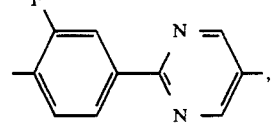
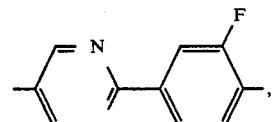
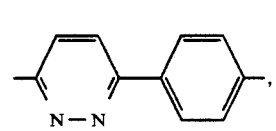
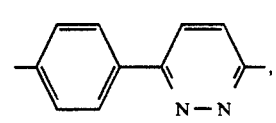
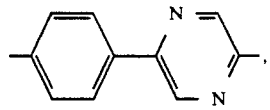
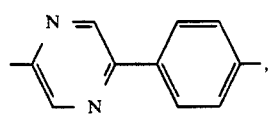
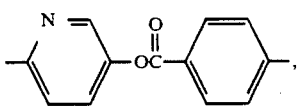
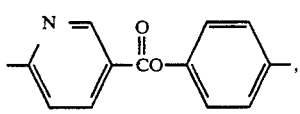
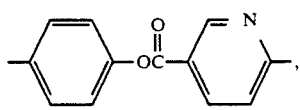
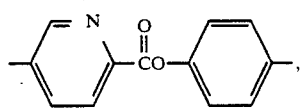
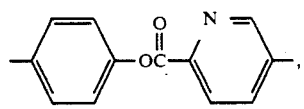
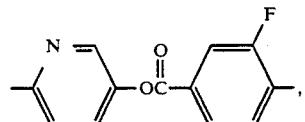
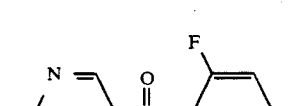
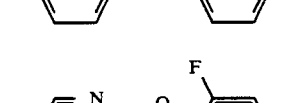
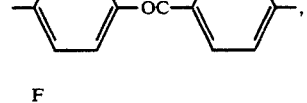
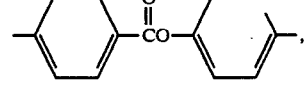
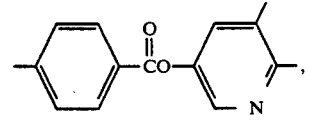

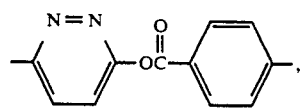
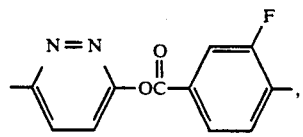
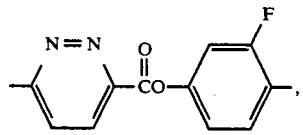
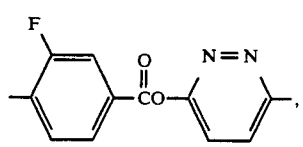
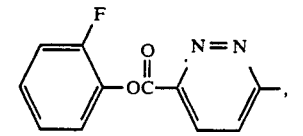
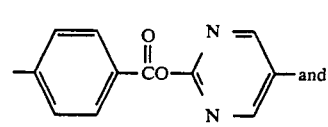
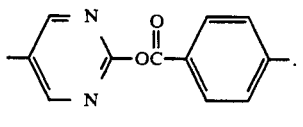

The process for preparing the optically active compound of the present invention will now be described.

The intermediate for use in preparing the compound of the present invention [compound of formula (1)] is prepared according to the following process.

An optically active aliphatic alcohol or carboxylic acid in which p is not zero can be synthesized according to the process using optically active β-hydroxyisobutyric acid as the starting compound.

In the following reaction formula, DHP represents dihydropyrene, p-TsOH represents p-toluenesulfonic acid, and THP represents a tetrahydropyranyl group.

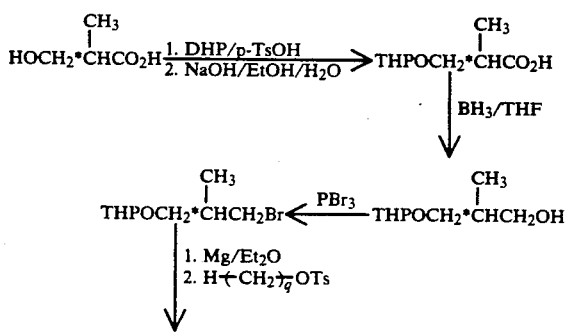

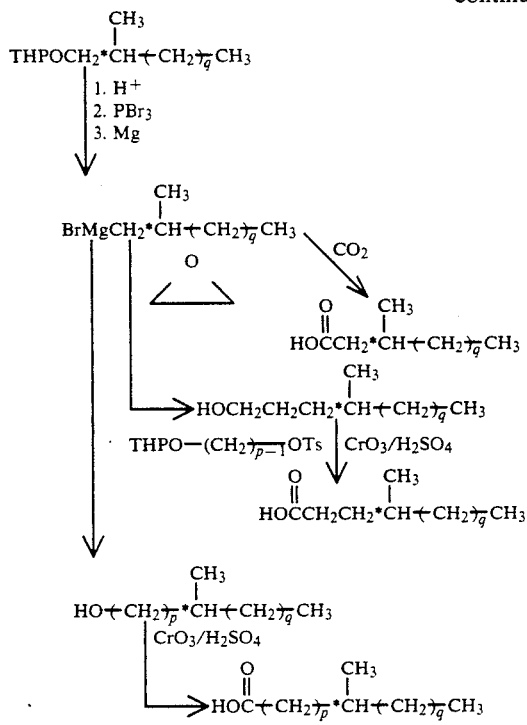

A corresponding optically active compound in which p is 0 is obtained by asymmetric reduction of a methyl alkyl ketone as described below with baker's yeast according to the following reaction:

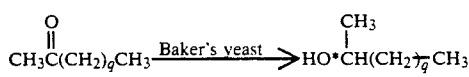

A 3-hydroxy-6-alkyl-δ-valerolactone is prepared according to the following process.

Namely, an optically active β-hydroxycarboxylic acid is prepared, for example, by reacting a methyl alkyl ketone with diethyl carbonate in the presence of sodium hydride to form an ethylene β-ketocarboxylate, hydrolyzing this ethyl ester and asymmetrically reducing the carbonyl group at the β-position with baker's yeast, as represented by the following reaction formula:

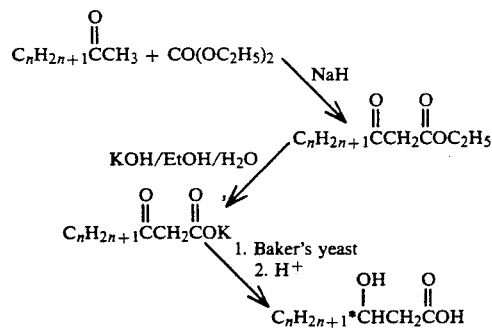

When the number of carbon atoms (n) in the alkyl group of the methyl alkyl ketone is not larger than 3, an alkyl ester of β-ketocarboxylic acid having a larger number of carbon atoms (at least 6) is preferably reduced instead of the ethyl β-ketocarboxylate, because the yield of the optically active compound can be further increased.

Separately, optically active monoethyl α-acetoxymalate is obtained by reacting S-(−)-malic acid with acetyl chloride and reacting the obtained product with absolute ethanol according to the following reaction formula [see Tetrahedron, 41, No. 13, 2751-2758 (1985)]:

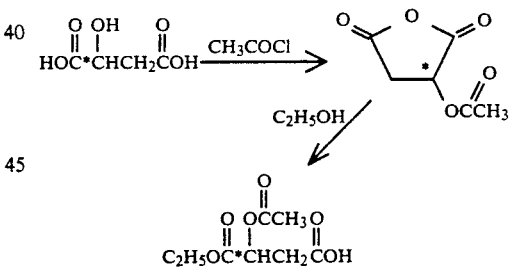

The obtained optically active β-hydroxycarboxylic acid and the optically active monoethyl ester of the α-acetoxy-dibasic acid are subjected to the Kolbe electrolysis as represented by the following reaction formula:

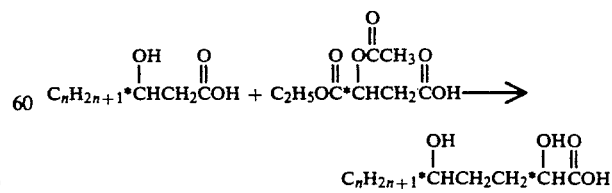

and the obtained product is cyclized in the presence of p-toluenesulfonic acid to obtain the above-mentioned valerolactone derivative according to the following reaction formula:

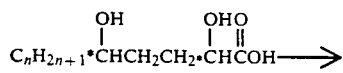
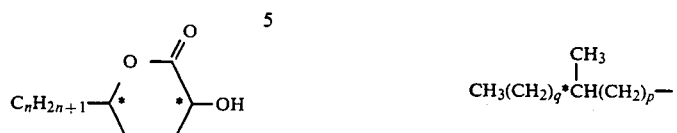

The synthesis of the compound represented by general formula (1) will now be described.

The compound represented by general formula (1) can be synthesized through the following routes.

(a) Compound of general formula (1) in which R* is $$CH_3(CH_2)_q \overset{*}{C}H(CH_2)_p-$$
$$\quad\quad\quad |$$
$$\quad\quad\quad CH_3$$

(a-1) In the case of $Z_1 = -CO_2-$, the following reaction is adopted:

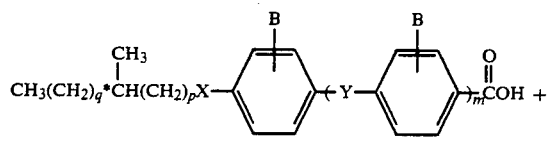

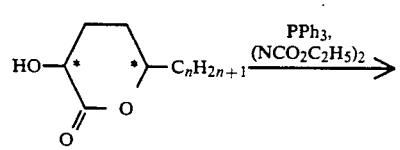

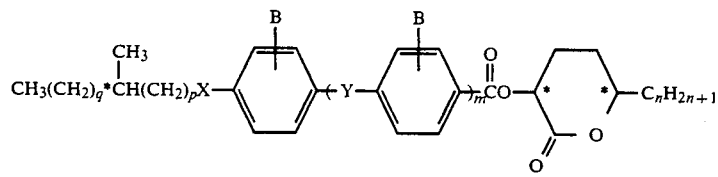

(a-2) In the case of $Z_1 = -O-$, the following reaction is adopted:

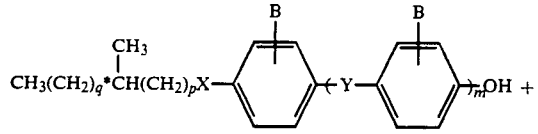

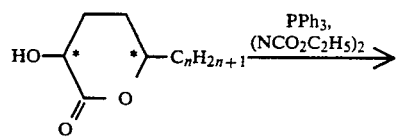

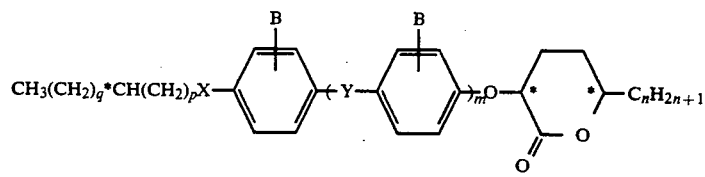

(a-3) In the case of $Z_1 = -CH_2O-$, the following reaction is adopted:

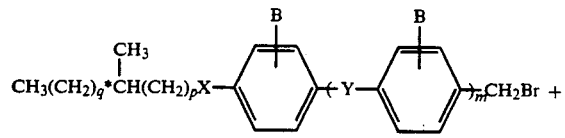

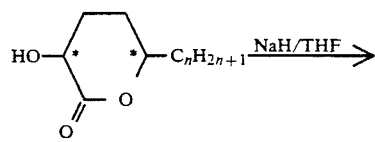
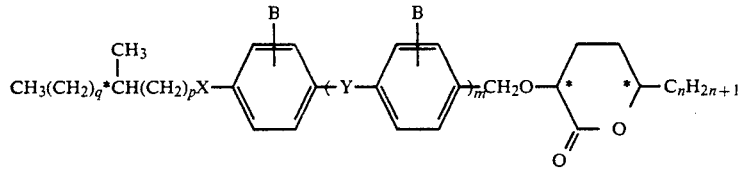
(b) Compound of general formula (1) in which R* is
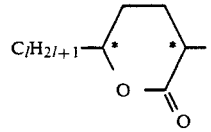
(b-1) In the case of X=—O—, $Z_1$=—O— and m=0, the following reaction is adopted:
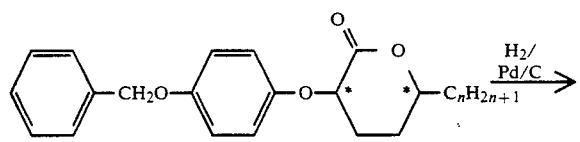
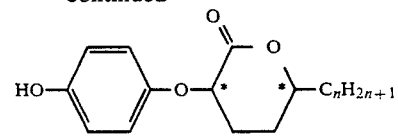
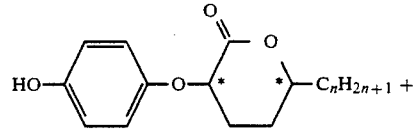
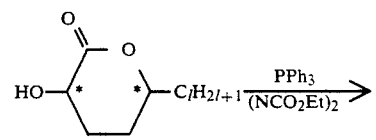
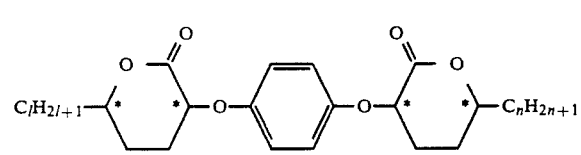
(b-2) In the case of
$$X = -O\overset{O}{\underset{\|}{C}}-,$$
$Z_1$ =—O— and m=0, the following reaction is adopted:
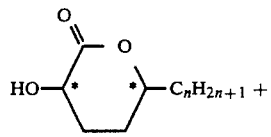
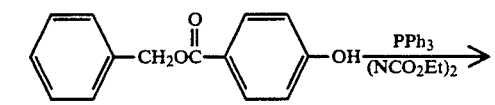
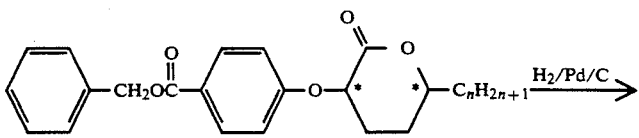

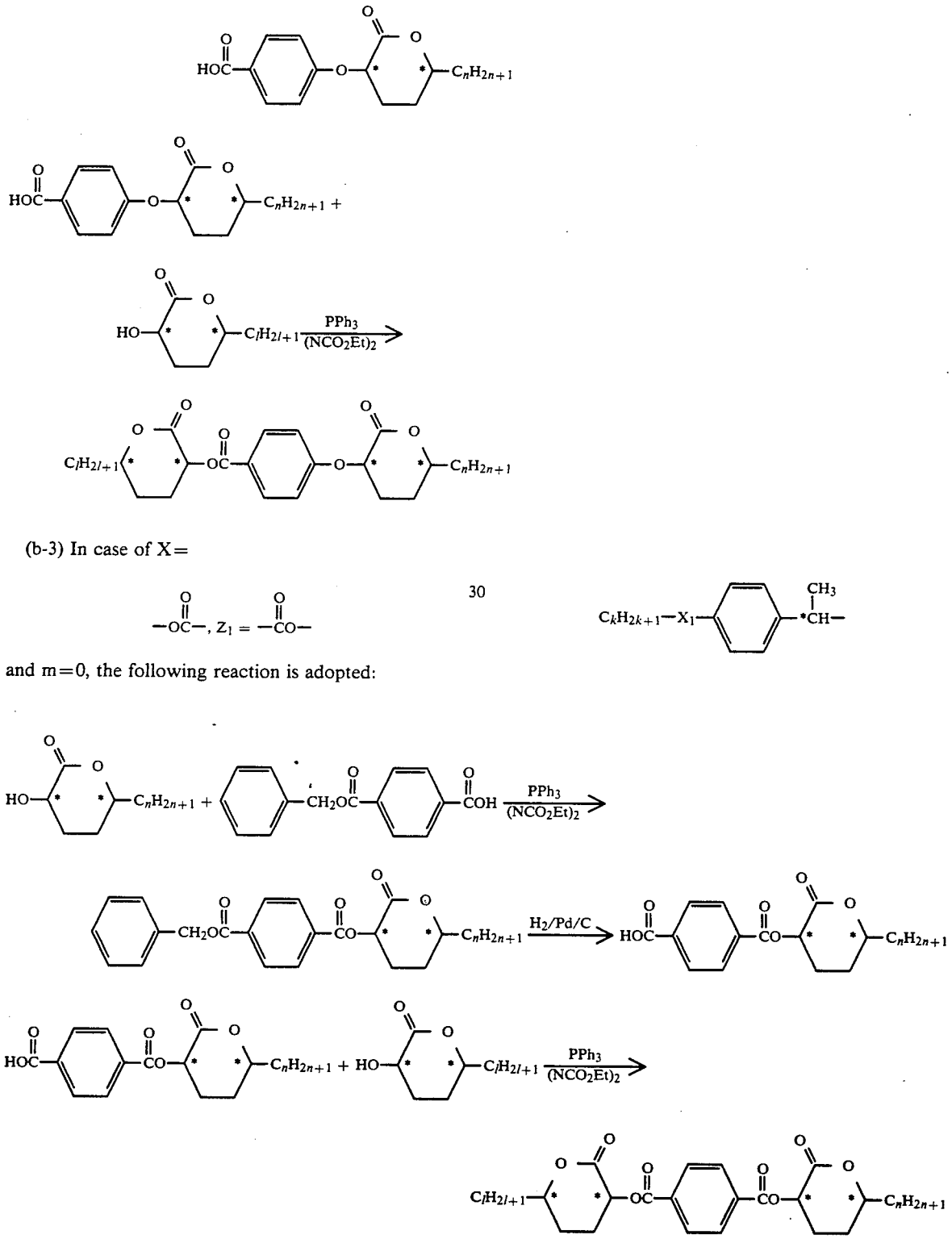
(b-3) In case of X = $-O\overset{O}{\overset{\|}{C}}-$, $Z_1 = -\overset{O}{\overset{\|}{C}}O-$
and m=0, the following reaction is adopted:
(c-1) In the case of X=—O—, m=0 and $Z_1 = -\overset{O}{\overset{\|}{C}}O-$, the following reaction is adopted:
(c) Compound of general formula (1) in which R* is

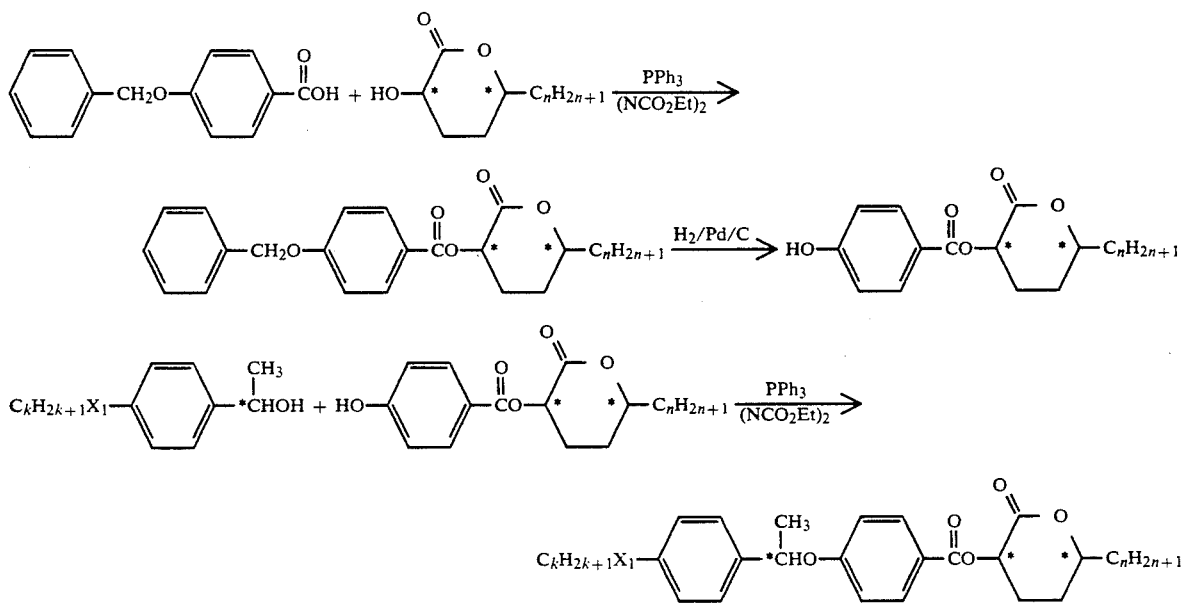
(c-2) In the case of X=—OCH$_2$—, m=0 and
$$Z_1 = -\overset{O}{\underset{\|}{C}}O-,$$
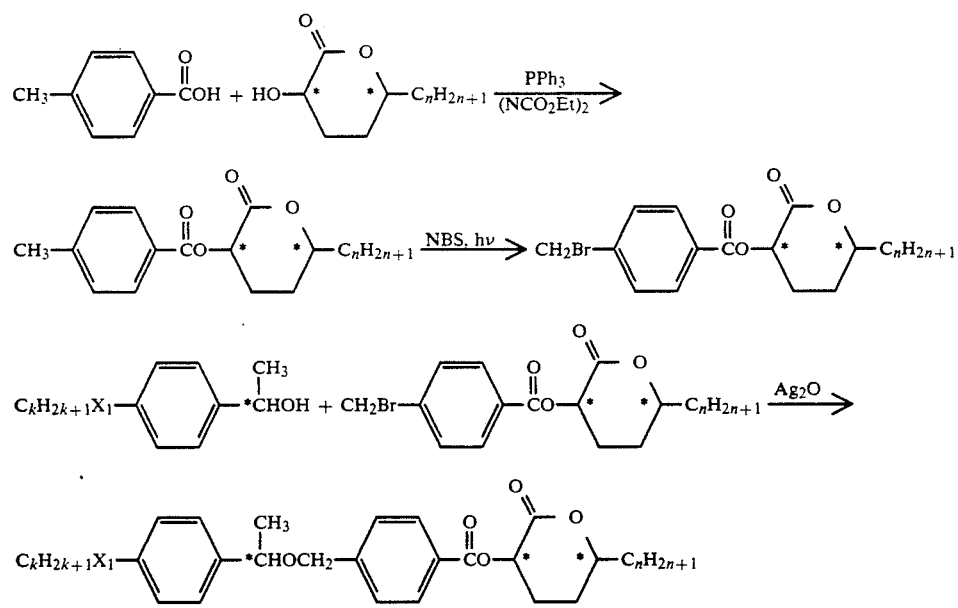
(c-3) In the case of X=
$-O\overset{O}{\underset{\|}{C}}-,$ m=0 and
the following reaction is adopted:
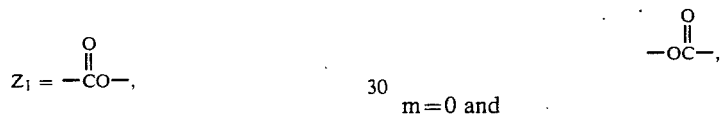
$$Z_1 = -\overset{O}{\underset{\|}{C}}O-,$$
the following reaction is adopted:
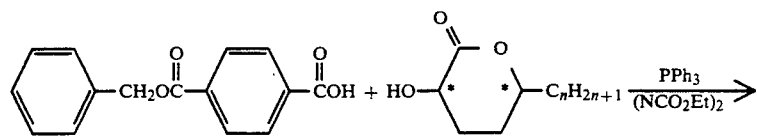

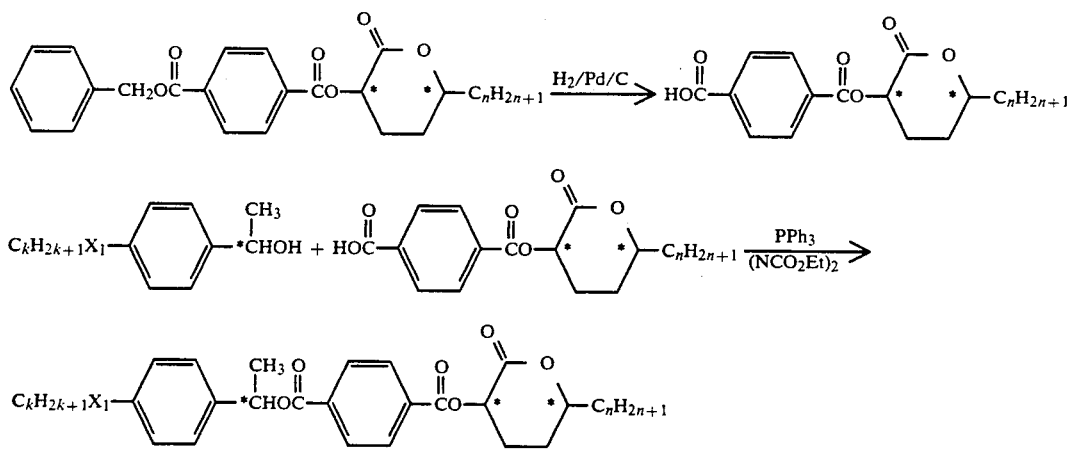

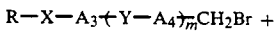

The compound of the present invention represented by formula (2) can be synthesized according to the following process.

(a) In the case of $Z_2 = -O-$, the following reaction is adopted:

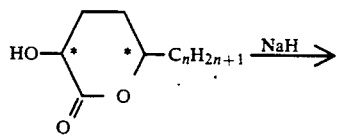

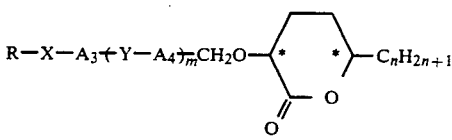

(b) In the case of $$Z_2 = -\overset{O}{\underset{\|}{C}}O-,$$

the following reaction is adopted:

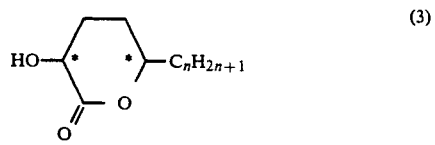

(c) In the case of $Z_2 = -CH_2O-$, the following reaction is adopted:

$R-X-A_3(Y-A_4)_{\overline{m}}CH_2Br +$

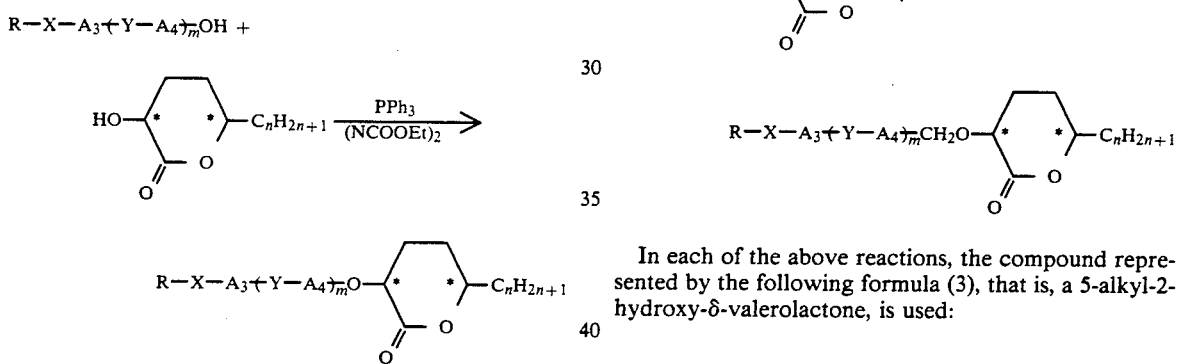

In each of the above reactions, the compound represented by the following formula (3), that is, a 5-alkyl-2-hydroxy-δ-valerolactone, is used:

(3)

The compound of formula (3) can also be synthesized through the following synthesis routes.

Namely, when optically active α-hydroxyglutaric acid-γ-lactone is used as the starting compound, the compound of formula (3) can be synthesized through the following synthesis route:

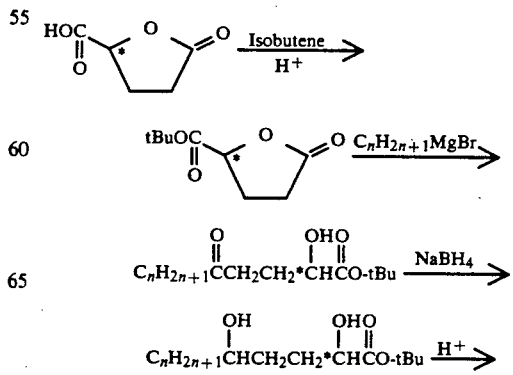

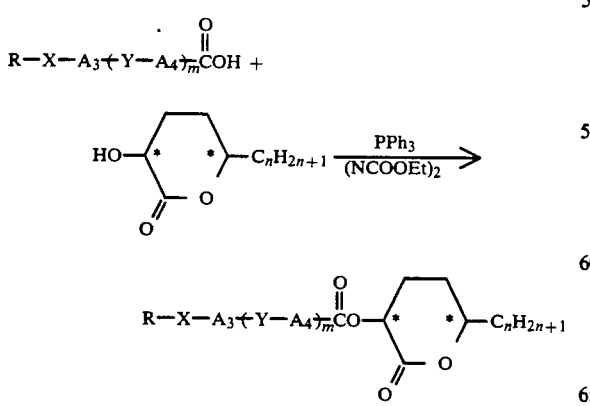

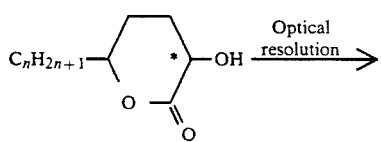

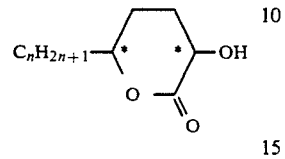

When 1,2,4-butanetriol is used as the starting compound, the compound of formula (3) can be synthesized through the following synthesis route:

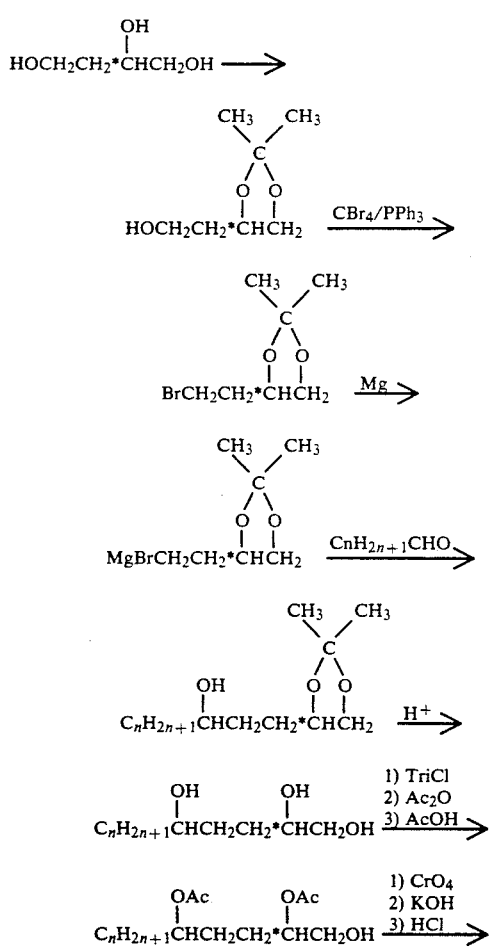

In the above reaction formula, TriCl represents triphenylmethane chloride.

When 1,2,4-butanetriol is used as the starting compound, the compound of formula (3) can also be synthesized according to the following process:

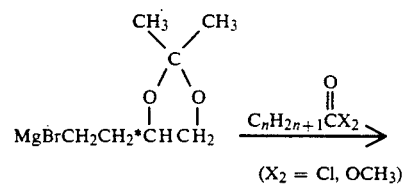

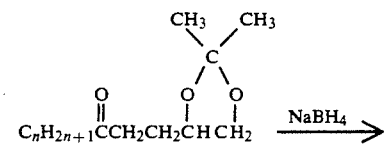

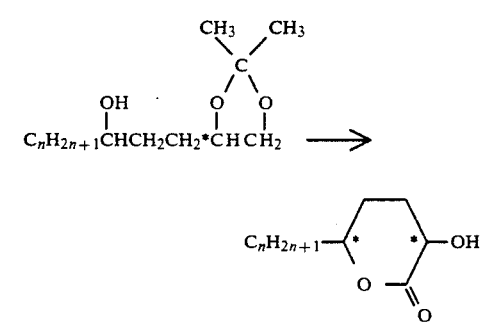

When an optically active alkane-1,2-epoxide is used as the starting compound, the compound of formula (3) can be prepared according to the following process:

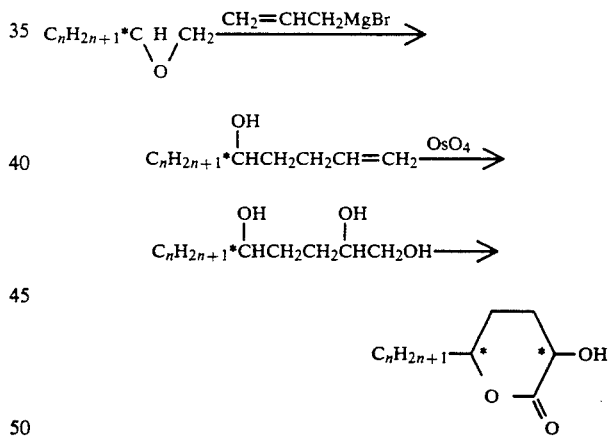

When D-mannitol is used as the starting compound, the compound of formula (3) can be synthesized according to the following process:

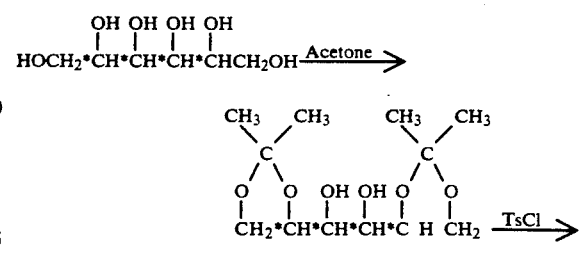

(in which TsCl represents tosyl chloride and Ts represents a tosyl group)

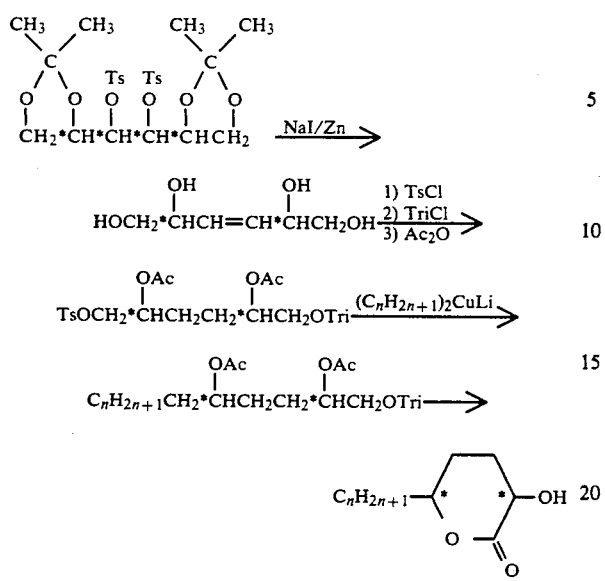

Of the compounds of the present invention, a compound in which a halogen atom or a cyano group is contained in $A_1$, $A_2$, $A_3$ or $A_4$ has a broad range of temperatures showing the Sm*C phase and a melting point lower than that of the compound not containing a halogen atom or a cyano group.

Since the compound of the present invention does not contain an azomethine bond which is possessed by the conventional ferroelectric liquid crystal compounds, the chemical stability such as the hydrolysis resistance is improved and the light stability is improved over the cinnamic acid type compounds. Accordingly, the compound of the present invention has good characteristics as a display material.

Some of the compounds included within the scope of the present invention do not show the chiral smectic C phase (Sm*C phase) when used alone. However, when these compounds are added to other liquid crystal materials having the SmC phase, that is, non-chiral liquid crystals exhibiting the phase series of isotropic phase (iso phase)-nematic phase (N phase)-smectic A phase (SmA phase)-smectic C phase (SmC phase) or isotropic phase-N phase-SmC phase or mixtures thereof in amounts such that the liquid crystal properties are not destroyed, they show an effect of inducting the ferroelectric phase (Sm*C phase). Therefore, even a compound of the present invention not showing the liquid crystal phase can be used as a preferable additive when a ferroelectric liquid crystal composition is prepared. The compound of the present invention is incorporated preferably in an amount of 1 to 90 mole % based on the liquid crystal composition.

In the compound of the present invention, the following effects can be attained by the synergistic action of the δ-valerolactone ring and the optically active branched alkyl chain.

(1) By adjusting the spontaneous polarization originating in the δ-valerolactone ring and the spontaneous polarization originating in the optically active branched alkyl chain, the intensity of the spontaneous polarization can be varied without changing the phase series or thermal properties.

(2) By increasing the spontaneous polarization, the response time can be shortened.

The liquid crystal composition of the present invention will now be described.

The liquid crystal composition of the present invention comprises at least one compound represented by formula (1) or (2). A composition comprising a plurality of ferroelectric liquid crystals compounds, optionally with other additive compounds, is advantageous over a composition comprising one ferroelectric liquid crystal compound alone, because the range of applicable temperatures can be broadened. Moreover, since compounds having a large tilt angle and compounds having a small tilt angle are included within the scope of the present invention, if these compounds are appropriately selected and mixed at an appropriate mixing ratio, a composition having a desirable tilt can be obtained. Therefore, the present invention is advantageous in that a composition suitable for a birefringence type display element and a composition suitable for a host-guest type display element can be freely prepared.

As examples of other ferroelectric liquid crystal compounds that can be mixed with at least one compound represented by general formula (1) or (2), compounds having a structure shown below can be used:

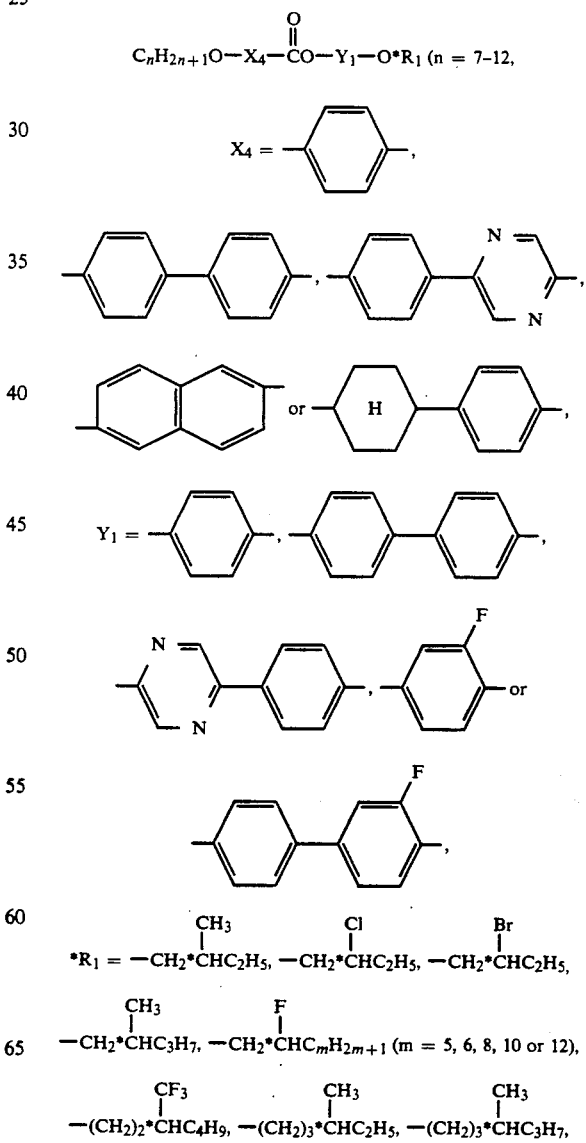

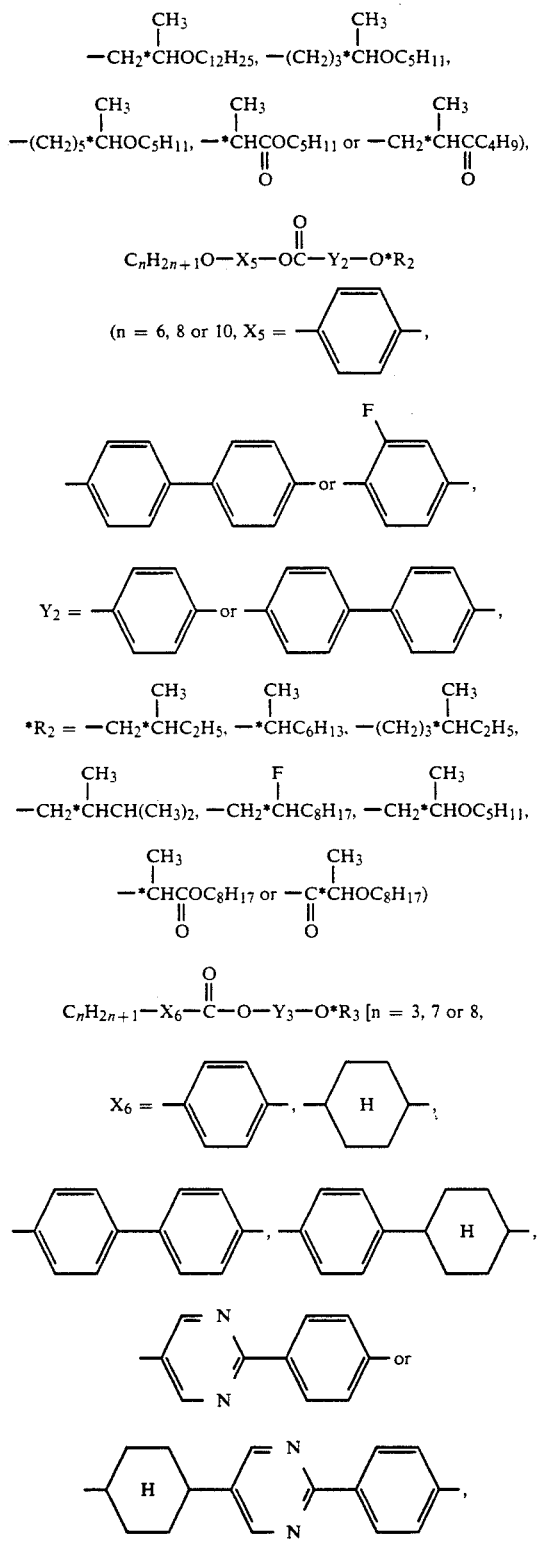
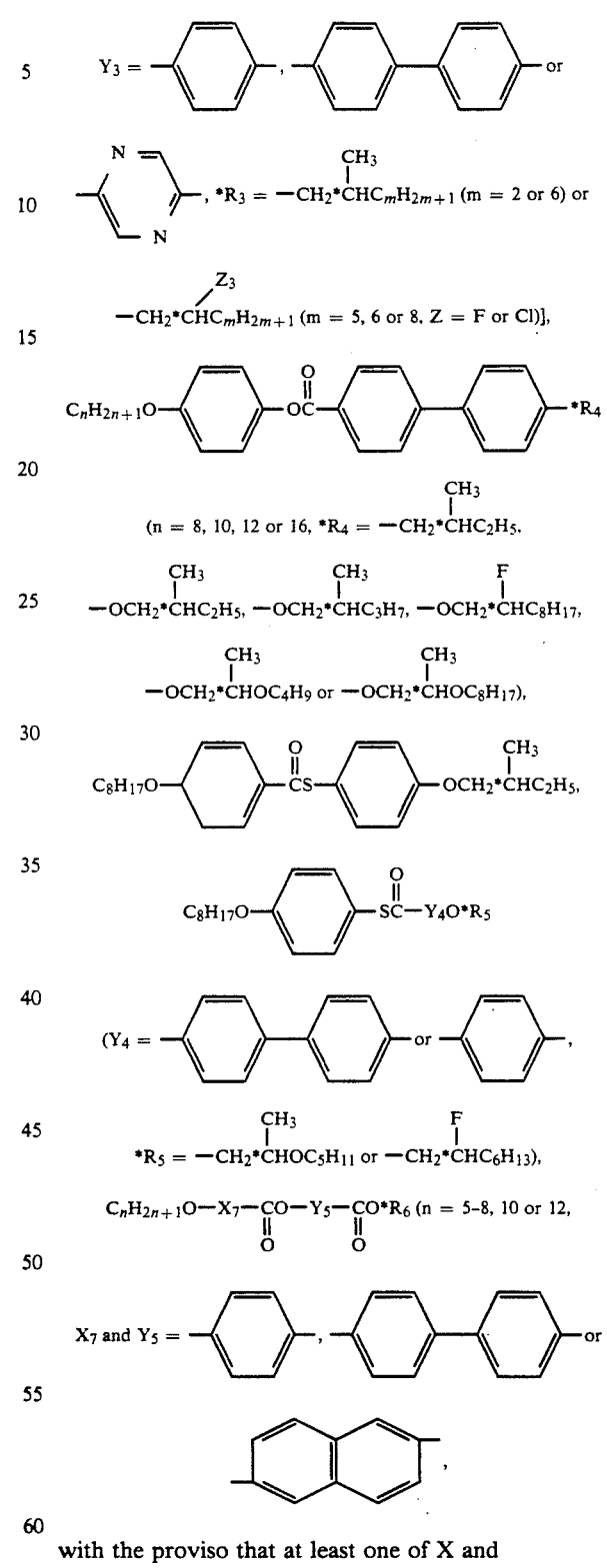

-continued $-*\text{CHC}_6\text{H}_{13}$, $-*\text{CHOC}_2\text{H}_5$ or $-*\text{CHCH}_2\text{COOC}_2\text{H}_5$), $C_nH_{2n+1}O-X_8-\overset{O}{\underset{\|}{C}}O*R_7$ (n = 5, 7, 8 or 12,

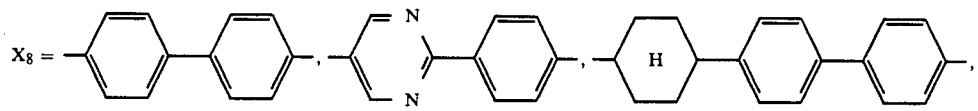

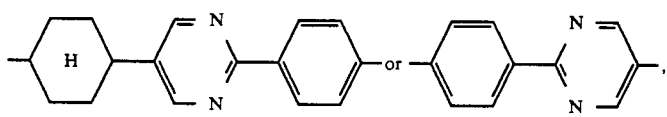

*$R_7 = -(CH_2)_3*CHC_2H_5$, $-CH_2*CHC_6H_{13}$, $-CH_2*CHC_8H_{17}$ or $-*CHC_8H_{17}$),

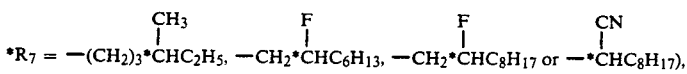

$R_1'-X_9-O*R_8(R_1' = -C_8H_{17}, -C_9H_{19}, -C_{10}H_{21}, -OC_{10}H_{21}$ or $-C_{11}H_{23}$, $X_9 =$ 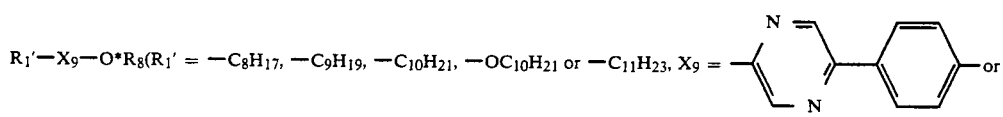

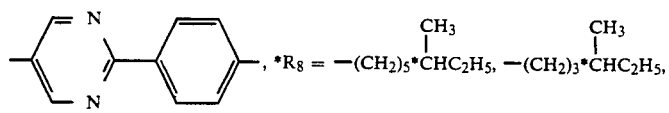, *$R_8 = -(CH_2)_5*CHC_2H_5, -(CH_2)_3*CHC_2H_5,$ $-(CH_2)_2*CHC_2H_5, -(CH_2)_3*CHOC_5H_{11}, -(CH_2)_5*CHOC_5H_{11}, -(CH_2)_3*CHOC_3H_7,$ $-(CH_2)_2*CHOC_{12}H_{25}, -CH_2*CHOC_3H_7, -CH_2*CHC_6H_{13}, -CH_2*CHC_8H_{17}$ $-(CH_2)_2*CHC_2H_5, -(CH_2)_2OCH_2*CHC_2H_5, -CH_2OCH_2*CHC_8H_{17},$ or $-(CH_2)_4OCH_2*CHC_6H_{13}$), $C_nH_{2n+1}-X_{10}-O$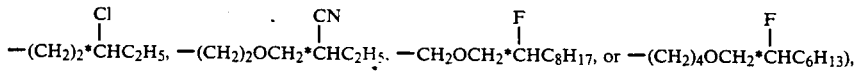$O*R_9$ (n = 8, 10 or 12, $X_{10} =$ 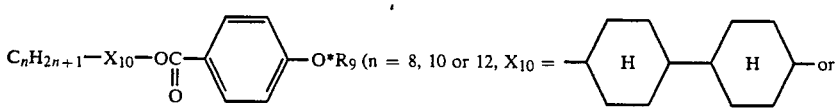

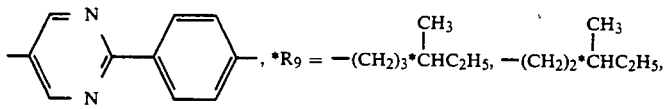, *$R_9 = -(CH_2)_3*CHC_2H_5, -(CH_2)_2*CHC_2H_5,$ $-(CH_2)_2*CHC_2H_5, -CH_2*CHC_6H_{13}$ or $-CH_2*CHC_4H_7$), $R_2'-X_{11}-OCH_2Y_6-*R_{10}$ ($R_2' = -C_2H_5, -C_{10}H_{21}, -OC_6H_{13}, -OC_7H_{15}, -OC_8H_{17}, -OC_{10}H_{21}$ or $-OC_{12}H_{25}$, $X_{11} =$ 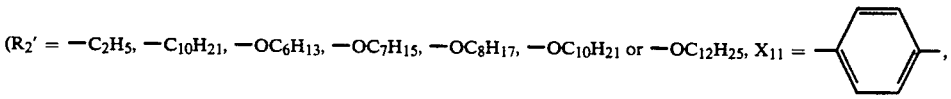,

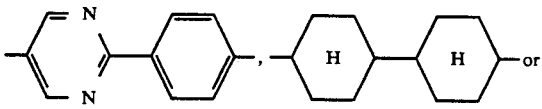

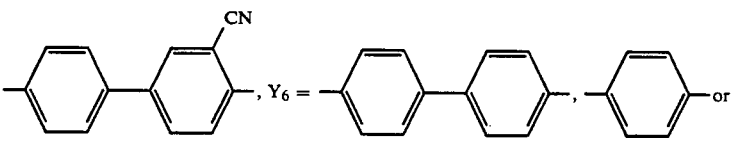, $Y_6 =$

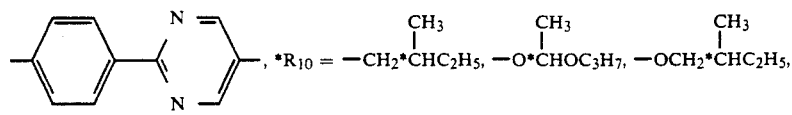, *R$_{10}$ = —CH$_2$*CHC$_2$H$_5$, —O*CHOC$_3$H$_7$, —OCH$_2$*CHC$_2$H$_5$, —O(CH$_2$)$_5$*CHOC$_3$H$_7$, —CO(CH$_2$)$_2$*CHC$_2$H$_5$, —O*CHCOC$_6$H$_{13}$, —O(CH$_2$)$_2$*CHC$_2$H$_5$, —OCH$_2$*CHC$_4$H$_9$, —CH$_2$CH$_2$COCH$_2$*CHC$_4$H$_9$ or —OCH$_2$*CHC$_6$H$_{13}$), R$_3'$—X$_{12}$—CH$_2$O—Y$_7$—*R$_{11}$ [R$_3'$ = C$_{10}$H$_{21}$O— or C$_n$H$_{2n+1}$—(n = 4, 6, 7 or 8), X$_{12}$ = 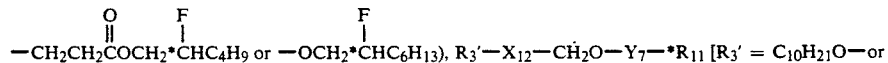,

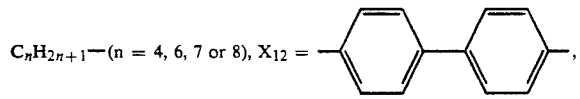,

Y$_7$ = 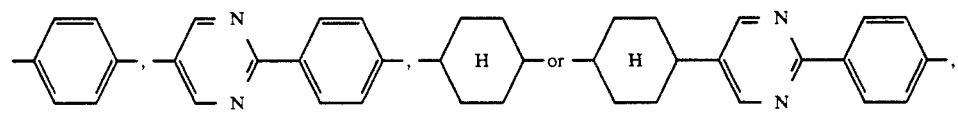,

*R$_{11}$ = —OCH$_2$*CHC$_2$H$_5$, —OCH$_2$*CHC$_5$H$_{11}$, —O(CH$_2$)$_3$*CHC$_5$H$_{11}$, —O(CH$_2$)$_3$*CHOC$_5$H$_{11}$,

—O(CH$_2$)$_2$*CHOC$_3$H$_7$, —O*CHCH$_2$OC$_2$H$_5$, —OCH$_2$*CHC$_7$H$_{15}$, —O*CHCOC$_3$H$_7$, —O*CHCOC$_6$H$_{13}$,

—CCH$_2$*CHC$_2$H$_5$, —C(CH$_2$)$_2$*CHC$_2$H$_5$, —OCCH$_2$*CHC$_2$H$_5$, —OCOCH$_2$*CHC$_2$H$_5$, —CH$_2$OCH$_2$*CHC$_{10}$H$_{21}$,

—CH$_2$OC*CHC$_3$H$_7$, —CH$_2$COCH$_2$*CHC$_5$H$_{11}$ or —(CH$_2$)$_2$OCCH$_2$*CHC$_2$H$_5$),

C$_n$H$_{2n+1}$—X$_{13}$OC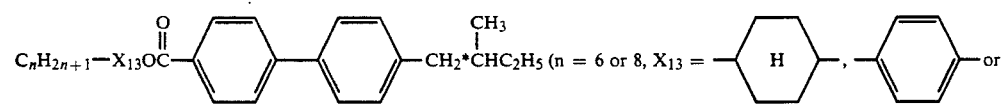CH$_2$*CHC$_2$H$_5$ (n = 6 or 8, X$_{13}$ = 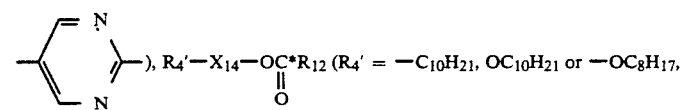 or

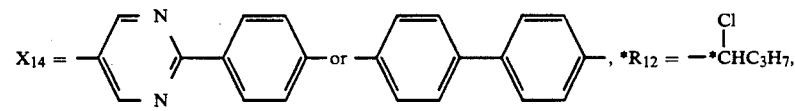), R$_4'$—X$_{14}$—OC*R$_{12}$ (R$_4'$ = —C$_{10}$H$_{21}$, OC$_{10}$H$_{21}$ or —OC$_8$H$_{17}$, X$_{14}$ = 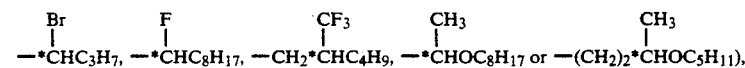, *R$_{12}$ = —*CHC$_3$H$_7$, —*CHC$_3$H$_7$, —*CHC$_8$H$_{17}$, —CH$_2$*CHC$_4$H$_9$, —*CHOC$_8$H$_{17}$ or —(CH$_2$)$_2$*CHOC$_5$H$_{11}$), C$_n$H$_{2n+1}$OC—X$_{15}$—OC—Y$_8$—O*R$_{13}$ (n = 6 or 10, X$_{15}$ = 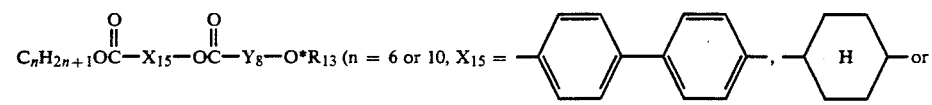

-continued
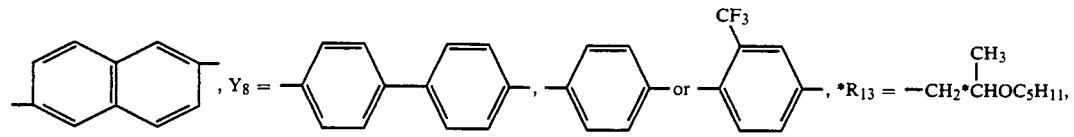
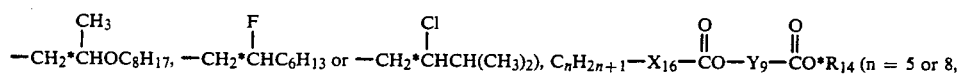
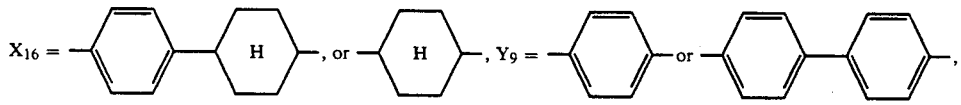
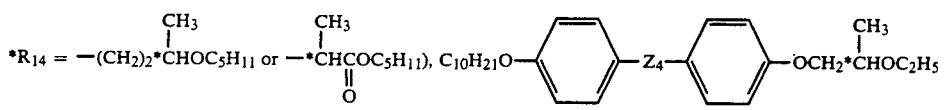
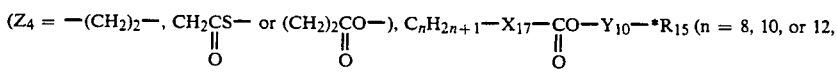
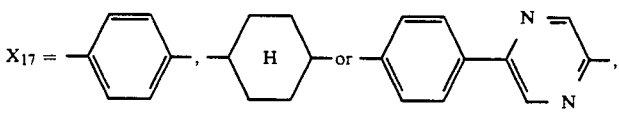
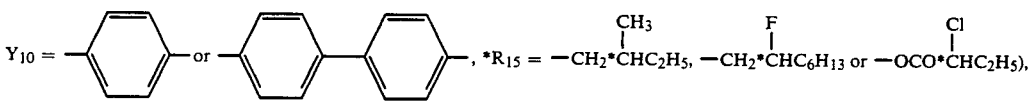
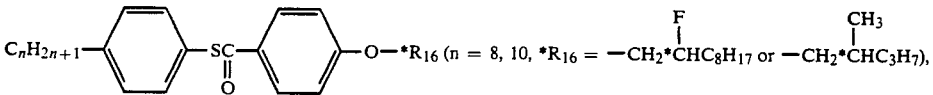
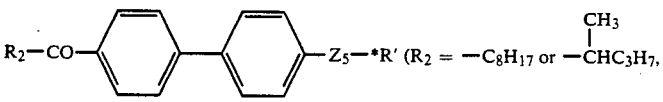
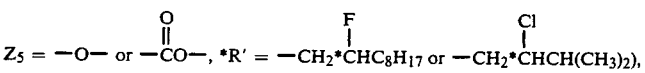
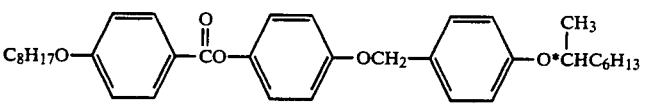
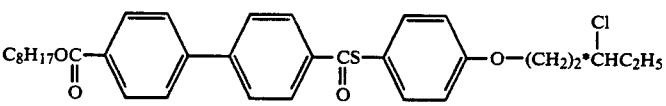
$C_mH_{2m+1}-X_{18}-C_nH_{2n+1}$ (m and n = 4-16,
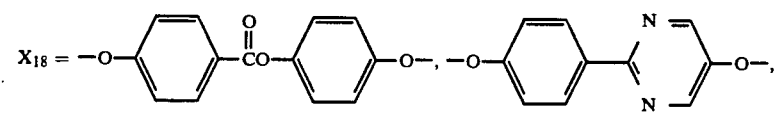
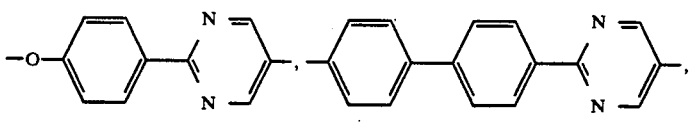

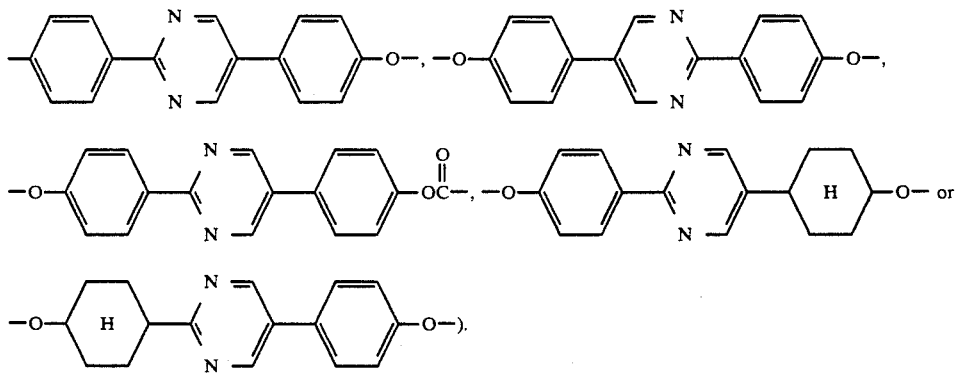

Other ferroelectric liquid crystal compounds can be used in the state mixed with the compound of formula (1) or (2).

Furthermore, when the compound of the present invention is mixed with a non-ferroelectric liquid crystal compound showing the SmC phase or a composition comprising non-ferroelectric liquid crystal compound, the mixture is a ferroelectric liquid crystal, and the mixture has a large spontaneous polarization, as is apparent form a short response time, and the mixture is very valuable.

Still further, the compound of the present invention is characterized in that zigzag defects often observed in conventional ferroelectric liquid crystals are reduced.

The liquid crystal composition of the present invention is advantageously used for a transmission type ferroelectric liquid crystal display, a reflection type ferroelectric liquid crystal display, a multicolor liquid crystal projection display, a parallel computing element, a space modulation element, a printer head, a light valve, an optical IC card, an optical memory/optical recording element, an E/O element, a steric display device and the like. Especially when the liquid crystal compound is used for various display devices, a light valve, an optical memory/optical recording element and a steric display device, the characteristic property of reduced zigzag defects is effectively utilized. Moreover, when the liquid crystal composition of the present invention is used for various computing elements, an E/O element, a printer head and a light valve, the characteristic property of a short response time is advantageously exerted.

The present invention will now be described in detail with reference to the following examples.

REFERENTIAL EXAMPLE 1

Synthesis of β-hydroxynonanoic acid

A solution of 20.0 g of methyl ethyl ketone in 100 ml of dioxane was added dropwisely into a solution comprising 210 ml of diethyl carbonate, 12.8 g of sodium hydride dispersed in an oil at a concentration of 60% by weight and 100 ml of dioxane in an argon atmosphere, the mixture was refluxed overnight, and the solvent was removed by distillation. The residue was subjected to distillation under reduced pressure to obtain 20.0 g of ethyl hexylketoacetate. The yield was 62.5% and the boiling point was 83° C. at 0.65 mmHg.

Then 15 g of the obtained ethyl hexylketoacetate was dissolved in a solution comprising 75 ml of ethanol, 75 ml of distilled water, and 5.02 g of potassium hydroxide, and the solution was stirred at room temperature for 7.5 hours. Then, 3 l of distilled water, 360 g of sucrose, and 168 g of dry yeast were added to the solution, and the mixture was shaken at 30° C. for 16 hours and filtered through Celite. The obtained solid was air-dried and extracted with ethyl acetate, and the extract was concentrated. Hydrochloric acid was added to the filtrate so that the pH value was 1, and sodium chloride was added to the filtrate to form a saturated solution and the solution was extracted with chloroform. The obtained extract and the abovementioned ethyl acetate extract concentrate were dissolved in diethyl ether. The solution was extracted two times with a 1N aqueous solution of sodium hydroxide. Hydrochloric acid and sodium chloride were added again to this aqueous solution to form a saturated aqueous solution of sodium chloride having a pH value of 1. The solution was extracted five times with ether, and the ether phase was recovered, washed with a saturated aqueous solution of sodium chloride, and dehydrated on magnesium sulfate. Ether was evaporated, and the residue was dissolved in n-hexane and recrystallized therefrom to obtain 7.81 g of β-hydroxynonanoic acid [melting point=49.3° to 50.0° C., $[\alpha]^{24.5} = -20.1°$ (C=1.1, CHCl$_3$)].

REFERENTIAL EXAMPLE 2

Synthesis of β-hydroxybutanoic acid

In a liquid comprising 36 ml of absolute ethanol and 36 ml of anhydrous 1,2-dichloroethane was suspended 5 g of optically active poly-β-hydroxybutyrate, and 1.1 ml of concentrated sulfuric acid was added to the suspension and the mixture was heated and refluxed. The mixture was cooled, a saturated aqueous solution of sodium chloride was added to the mixture, Celite was suspended in the mixture and filtration was carried out. The filtrate was extracted once with 70 ml of ether and three times with 20 ml of ether, and the residue was washed with 100 ml of ether. The ether used for the washing was combined with the extract, and the mixture was washed with a saturated solution of sodium hydrogencarbonate and a saturated aqueous solution of sodium chloride and then dried on magnesium sulfate. After the drying, the ether was removed and the residue was subjected to distillation under reduced pressure to obtain 4.0 g of ethyl (R)-β-hydroxybutanoate ($[\alpha]^{21.5} = +43.9°$).

In a liquid mixture comprising 15 ml of water, 15 ml of ethanol and 1.6 g of sodium hydroxide was dissolved 4.0 g of the obtained ethyl (R)-β-hydroxybutanoate, and the solution was heated and refluxed for 3 hours, and then cooled and ion-exchanged with an ion exchange resin (Amberlite R120B supplied by Rohm & Haas). The solvent was removed by dilstillation under reduced pressure to obtain 3.6 g of β-hydroxybutanoic acid.

REFERENTIAL EXAMPLE 3

Synthesis of 1-ethyl S-(2)-acetoxybutanedioate of the following formula

To 50 g of (s)-(—)-malic acid was added 160 ml of acetyl chloride, the mixture was stirred and refluxed at 55° C. for 4 hours, and the solution was concentrated in vacuo. Then 100 ml of benzene was added to the residue and benzene and acetic acid were removed by distillation in vacuo. The concentrate was cooled to room temperature and 100 ml of absolute ethanol was added thereto. The mixture was violently stirred while intermittently cooling the mixture. Then the mixture was heated at 70° to 75° C. for 10 minutes and at 50° to 55° C. for 10 hours. The solvent was removed from the mixture by distillation under reduced pressure, and the residue was separated and purified in a silica gel column by using methylene chloride/methanol (50/1) as the developing solvent to obtain 50.9 g of 1-ethyl S-(2)-acetoxybutanedioate [melting point=50° to 51° C., $[\alpha]^{23} = -31.6°$ (C=1.42, ethanol)].

REFERENTIAL EXAMPLE 4

Synthesis of (2S, 5R)-2-hydroxy-5-hexyl-δ-valerolactone of the following formula:

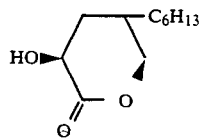

In methanol were dissolved 2.30 g of (R)-β-hydroxynonanoic acid synthesized in Referential Example 1 and 7.90 g of 1-ethyl S-(2)-acetoxybutanedioate synthesized in Referential Example 3, 230 mg of sodium methylate was added to the solution, and the Kolbe electrolysis was carried out under conditions of 20° to 30° C., 40 V and 1.5 A for 5 hours by using a constant voltage electrolysis apparatus (Model VE-8 supplied by Yanaco). After the electrolysis, 60 ml of a 3N aqueous solution of sodium hydroxide was added to the hydrolysis reaction mixture, the solution was stirred overnight, methanol was removed, and the residue was washed with ether. The alkaline aqueous solution layer was recovered and hydrochloric acid was added thereto so that the pH value was 1. Then sodium chloride was added to the liquid mixture to form a saturated aqueous solution of sodium chloride. This aqueous solution was extracted with chloroform, the extract was dehydrated on magnesium sulfate, and chloroform was evaporated. The residue left after the evaporation of chloroform was dissolved in 10 ml of benzene, a catalytic amount of p-toluenesulfonic acid was added to the solution, and the mixture was stirred at room temperature for 2 hours and dissolved in ether. The solution was washed three times with a saturated aqueous solution of sodium bicarbonate and once with a saturated aqueous solution of sodium chloride and then dehydrated on magnesium sulfate. The residue left after removal of ether by evaporation was developed with an n-hexane/ethyl acetate mixed solvent by using a silica gel column to separate and purify the target compound. Recrystallization from a n-hexane/ethyl acetate mixed solvent gave 700 mg of (2S, 5R)-2-hydroxy-5-hexyl-δ-valerolactone. The melting point was 75.5° to 77.0° C., and the elementary analysis values were as shown below.

Elementary analysis values
Found values: C=65.84%, H=10.29%, N=0.06%
Calculated values: C=76.32%, H=10.07%, N=0%
The specific rotatory power $[\alpha]^{25}$ was +76.8° (C=1.1 in chloroform). The results of the $^1$H-NMR analysis were as shown below.

$^1$-NMR, δ ppm: 4.36 (2H), 3.21 (1H), 1.31 (14H), 0.89 (3H)

When the above procedures were repeated in the same manner except that β-hydroxybutanoic acid synthesized in Referential Example 2 was used instead of (R)-β-hydroxynonanoic acid, (2S,5R)-2-hydroxy-5-methyl-δ-valerolactone was obtained.

REFERENTIAL EXAMPLE 5

Synthesis of 4-(S)-2-methylheptyloxybenzoic acid

In 50 ml of pyridine was dissolved 6.5 g of (R)-2-octanol, 9.5 g of p-toluenesulfonyl chloride was added to the solution under ice cooling, and the mixture was stirred overnight. Then 100 ml of hexane was added to the mixture, the precipitated crystal was removed by filtration, and the remaining hexane solution was washed with dilute hydrochloric acid and then with a saturated aqueous solution of sodium chloride and was then dehydrated on magnesium sulfate. Under reduced pressure, hexane was evaporated to effect concentration, whereby 11.2 g of (R)-2-octyl-p-toluenesulfonate was obtained. Then the obtained product and 5.1 g of 4-hydroxybenzoic acid were suspended in ethanol, 20 ml of a 3N aqueous solution of potassium hydroxide was added to the suspension, and reaction was carried out under reflux for 2 hours. The reaction mixture was cooled and made acidic by addition of hydrochloric acid, the mixture was extracted with benzene, and the extract was washed with a saturated aqueous solution of sodium chloride and dehydrated on magnesium sulfate. Benzene was removed by distillation and the obtained crude product was recrystallized from hexane/ethyl acetate to obtain 4.5 g of 4-(5)-2-methylheptyloxybenzoic acid.

REFERENTIAL EXAMPLE 6

Preparation of (2S,5R)-5-hexyl-2-hydroxy-δ-valerolactone from (S)-4-carboxy-γ-butyrolactone To 10 g of (S)-4-carboxy-γ-butyrolactone synthesized from L-glutamic acid by the process of D. L. Cotten [J.O.C., 534, 780–4786 (1988)] was added 20 ml of thionyl chloride, and the mixture was refluxed for 2 hours. The excess of thionyl chloride was removed by distillation under reduced pressure, the residue was dissolved in 20 ml of dry methylene chloride, the solution was added dropwise into a solution of 8 g of t-butanol and 10 g of pyridine in 10 ml of methylene chloride, and reaction was carried out at room temperature overnight. Water was added to the reacted solution and the methylene chloride solution was separated, washed with water and a saturated solution of copper sulfate and dried on magnesium sulfate. The solvent was removed from the methylene chloride solution, and the residue was purified by the silica gel column chromatography to obtain 15 g of butyl (S)-γ-butyrolactone-4-carboxylate.

Separately, 1.65 g of n-hexyl bromide distilled afresh was dissolved in 5 ml of tetrahydrofuran, and the solution was added dropwise into a tetrahydrofuran reacted solution containing 0.24 g of magnesium suspended therein in an argon atmosphere to form a Grignard reagent.

The formed Grignard reagent was cooled to −40° C. by dry ice/acetone, and a solution of 1.9 g of t-butyl (S)-γ-butyrolactone-4-carboxylate in 5 ml of tetrahydrofuran was added dropwise into the Grignard reagent. The mixture was stirred overnight while gradually elevating the reaction temperature to room temperature. Then 2 ml of a saturated solution of ammonium chloride was added to the reaction mixture, 50 ml of chloroform was added to the mixture, and the chloroform solution was separated. The chloroform solution was washed with a saturated aqueous solution of sodium chloride and dried on magnesium sulfate. The solvent was removed by distillation to obtain a crude product.

A solution of 0.4 g of NaBH$_4$ in 5 ml of isopropyl alcohol was added dropwise into an isopropanol solution (10 ml) of the obtained crude product with stirring, and the mixture was stirred overnight. The reacted solution was neutralized with dilute hydrochloric acid and extracted with 50 ml of chloroform. The obtained chloroform solution was dried on magnesium sulfate and the solvent was removed by distillation to obtain a crude product. The crude product was reacted with 10 ml of trifluoroacetic acid to hydrolyze the t-butyl ester. Then 10 ml of water and 20 ml of chloroform were added to the reacted solution and the organic phase was separated and dried on magnesium sulfate. Then the solvent was removed by distillation, and the obtained crude product was dissolved in 20 ml of benzene, and 0.1 g of p-toluenesulfonic acid was added to the solution and the mixture was refluxed for 2 hours. The obtained crude δ-valerolactone was purified by the silica gel column chromatography to obtain 0.8 g of (2S,5R)-2-hdyroxy-5-hexyl-δ-valerolactone.

The specific rotatory power $α_D$ of the obtained compound was +16° (C=1, CHCl$_3$) (20° C.). The NMR chart of the obtained compound is shown in FIG. 1.

The obtained compound was dissolved in benzene, and 0.8 g of 3,5-dinitrobenzoic acid chloride and 1 g of pyridine were added to the solution and esterification was carried out. The obtained product was purified by the silica gel chromatography to obtain 0.3 g of (2S,5R)-2-(3,5-dinitrophenylcarboxy)-5-hexyl-δ-valerolactone. The unreacted 2-hydroxy-5-hexyl-δ-valerolactone was recovered and recrystallization from pentane gave 0.1 g of (2S,5R)-2-hydroxy-5-hexyl-δ-valerolactone.

Figure 2:
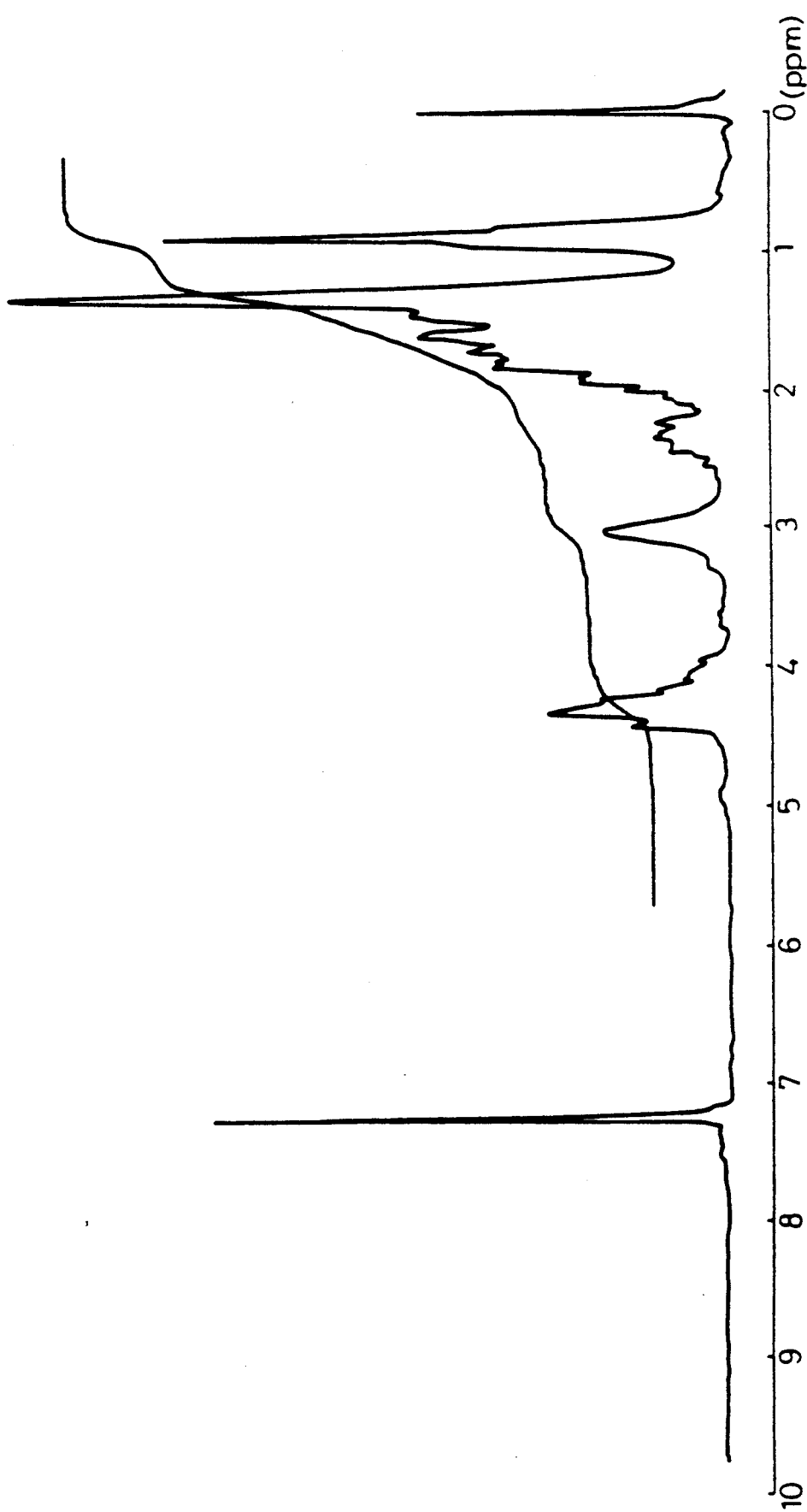
FIG. 2 shows the NMR spectrum of (2S,5R)-2-hydroxy-5-hexyl-δ-valerolactone.

The specific rotatory power $α_D$ of the obtained product was +76.8° (C=1.1, CHCl$_3$) (25° C.). The NMR chart of the product is shown in FIG. 2.

REFERENTIAL EXAMPLE 7

Preparation of (2S,5R)-2-hydroxy-5-hexyl-δ-valerolactone from (S)-(-)-1,2,4-butanetriol In 150 ml of acetone was dissolved 8.1 g of (S)-(-)-1,2,4-butanetriol, 0.05 g of p-toluene-sulfonic acid was added to the solution, and the mixture was stirred at room temperature overnight and neutralized with sodium hydrogencarbonate. The mixture was stirred for 20 minutes and filtered, and the filtrate was concentrated and distilled under a reduced pressure of 20 mmHg at 108° C. to obtain 8.6 g of an acetonide.

In 50 ml of dry dichloromethane was dissolved 5.2 g of triphenylphosphine, and the solution was added dropwise over a period of 4 hours into a solution of 2.9 g of the acetonide and 10 g of carbon tetrabromide in 4 ml of methylene chloride. The mixture was stirred at room temperature for 1 hour, 150 ml of n-pentane was added to the mixture, and the formed precipitate was recovered by filtration, washed with 50 ml of n-pentane and combined with the n-pentane solution. The mixture was washed with a solution of sodium hydrogencarbonate and with water, dried on magnesium sulfate and concentrated. The concentrate was subjected to distillation under reduced pressure to obtain 2.5 g of 1-bromobutane-2,4-diol-acetonide. Then 0.3 g of magnesium was placed in 10 ml of dry ether, and a Grignard reagent was prepared by dissolving the obtained bromination product in 10 ml of dry ether by customary procedures. A solution of 1.14 g of heptyl aldehyde distilled afresh in 5 ml of dry ether was added to the Grignard reagent at room temperature. The mixture was stirred overnight, and a saturated aqueous solution of ammonium chloride was added to the reaction liquid. The ether layer was separated and washed with a saturated aqueous solution of sodium chloride.

The washed ether solution was dried on magnesium sulfate, the solvent was removed by distillation, and the residue was purified by the silica gel column chromatography to obtain 2.1 g of (2S,5R)-1,2,5-undecanetriol-1,2-acetonide. The obtained product was dissolved in 10 ml of acetic acid and 5 ml of water and the solution was treated at 50° C. for 3 hours, neutralized with an aqueous solution of sodium hydrogen-carbonate, and extracted with chloroform. The chloroform solution was washed with a saturated aqueous solution of sodium chloride and dried on magnesium sulfate. The solvent was removed by distillation, the residue was dissolved in 20 ml of pyridine, 2.4 g of triphenylmethane chloride was added to the solution, and reaction was carried out overnight. Then 3 ml of acetic anhydride was added to the reacted solution and the mixture was further stirred overnight. Water was added to the reacted solution and the mixture was extracted with 50 ml of ethyl acetate. The obtained ethyl acetate solution was washed with a saturated aqueous solution of copper sulfate, water, a solution of sodium hydrogen-carbonate and then water, and the solution was dried on magnesium sulfate and the solvent was removed by distillation. The obtained crude product was purified by the silica gel column chromatography to obtain 4 g of (2S,5R)-2,5-diacetoxy-1-triphenylmethoxyundecane. The product was dissolved in 10 ml of acetic acid and 7 ml of water, and the solution was treated at 50° C. for 3 hours. The solution was cooled, the formed precipitate was removed by filtration, and the filtrate was concentrated under reduced pressure. The crude product was dissolved in 15 ml of acetone, and the solution was cooled to 0° C. and oxidized with 1.1 equivalents of Jones reagent. After the reaction was conducted for 20 minutes, isopropanol was added to the reacted mixture and the mixture was reacted with an excessive amount of Jones reagent. The majority of acetone was removed by distillation and the residue was extracted with 30 ml of chloroform. The chloroform solution was separated, washed with a saturated aqueous solution of sodium chloride, and dried on magnesium sulfate. The solvent was removed by distillation under reduced pressure, and deacetylation was carried out with 2.1 equivalents of potassium hydroxide-ethanol/water (1/1) solution. Then, the reacted solution was made acidic and extracted with chloroform. The chloroform solution was washed with a saturated aqueous solution of sodium chloride and dried on magnesium sulfate. The solvent was removed by distillation and the residue was dissolved in 20 ml of benzene, and 0.1 g of p-toluenesulfonic acid was added to the solution and the mixture was refluxed for 2 hours. The reacted solution was washed with a solution of sodium hydrogencarbonate, dried on magnesium sulfate and concentrated under reduced pressure. The crude product was purified by the silica gel chromatography to obtain 1.2 g of (2S,5RS)-2-hydroxy-5-hexyl-δ-valerolactone.

Then in the same manner as described in Referential Example 6, (2S,5R)-2-hydroxy-5-hexyl-δ-valerolactone was obtained.

When (2S,5R)-2-hydroxy-5-hexyl-δ-valerolactone was prepared from (2R)-octane-1,2-epoxide as the starting compound, a tetrahydrofuran solution of an aryl Grignard reagent was synthesized from an aryl bromide by the process disclosed in Organic Synthesis, V, 608 (1973), a tetrahydrofuran solution of (2R)-octane-1,2-epoxide was added thereto, and the mixture was refluxed and reacted in an argon atmosphere. A saturated aqueous solution of ammonium chloride was added to the reacted mixture, and the mixture was extracted with chloroform. The chloroform solution was separated, washed with a saturated aqueous solution of sodium chloride, and dried on magnesium sulfate and concentrated under reduced pressure to obtain a crude product. Osmium tetroxide was added to a solution of the crude product in anhydrous ether to effect reaction, and the precipitated osmic ester was recovered by filtration and shaken with mannitol, an aqueous solution of potassium hydroxide and chloroform. Crude (2RS,5R)-1,2,5-undecanetriol was obtained from the chloroform phase, and in the same manner as described above with respect to (2S,5RS)-1,2,5-undecanetriol, protecting reaction, oxidation, removal of the protecting group, cyclization and optical resolution were carried out to obtain (2S,5R)-2-hydroxy-5-hexyl-δ-valerolactone.

The intended compound was similarly obtained by using an arylphenyl sulfide instead of the Grignard reagent synthesized from the aryl bromide.

REFERENTIAL EXAMPLE 8

Preparation of (2S,5R)-2-hydroxy-5-hexyl-γ-valerolactone from D-mannitol

By the process disclosed in Carbohydrate Research, 84, 350-352 (1980), 20 g of 1,2,5,6-di-o-isopropylidene-D-mannitol was obtained from 25 g of D-mannitol. To the obtained compound were added 30 ml of pyridine and 29.1 g of p-toluenesulfonyl chloride, and reaction was carried out at 40° C. for 3 days. The reacted solution was poured into ice water, the insoluble substance was dissolved in chloroform and the solution was washed with an aqueous solution of sodium hydrogenocarbonate and a saturated aqueous solution of sodium chloride and dried on magnesium sulfate. The solvent was removed by concentration under reduced pressure and the residue was recrystallized from an acetone/methanol mixed solvent to obtain 29 g of 1,2,5,6-di-o-isopropylidene-3,4-ditosyl-D-mannitol. Then 21 g of the obtained compound was dissolved in 50 ml of dimethylformamide, and 16 g of sodium iodide and 12 g of powdery zinc were added to the solution and the mixture was refluxed with violent stirring for 5 hours. After cooling, the insoluble substance was recovered by filtration and washed with dimethylformamide, and water was added to the filtrate and the organic portion was extracted with chloroform. The chloroform solution was washed with a saturated aqueous solution of sodium chloride, dried and concentrated under reduced pressure. The crude product was recrystallized from methanol/water to obtain 5 g of (2R,5R)-3-hexene-1,2,5,6-tetraol-diacetonide. Then 1 g of the obtained compound was dissolved in 10 ml of ethanol, 0.1 g of palladium/carbon was added to the solution, and reduction was carried out at room temperature under a hydrogen pressures of 3 kg/cm$^2$ for 2 days. The catalyst was removed by filtration, and when the filtrate was concentrated, (2R,5R)-1,2,5,6-hexane-tetraol was quantitatively obtained. The obtained compound was dissolved in 5 ml of pyridine and 1 equivalent of p-toluenesulfonyl chloride was added to the solution, and reaction was carried out overnight. Then 1 equivalent of triphenylmethane chloride was added to the reacted mixture, and reaction was carried out overnight. Then an excessive amount of acetic anhydride was added to the reacted mixture and reaction was carried out overnight. The reacted solution was poured into water, and the precipitated organic substance was dissolved in ether and the ether solution was washed with water, a saturated aqueous solution of copper sulfate and then water, and dried on magnesium sulfate. Ether was removed by distillation and the residue was separated and purified by the silica gel column chromatography to obtain 1.5 g of (2R,5R)-2,5-diacetyl-1-tosyl-6-tritylhexane-tetraol.

A hexane solution of 2 equivalents of n-butyl lithium was added dropwise into a suspension of 1.37 g of copper iodide in 10 ml of anhydrous ether at −30° C. The mixture was cooled to 0° C. and a solution of 0.6 g of (2R,5R)-2,5-diacetyl-1-tosyl-6-tritylhexane-tetraol in 10 ml of anhydrous ether was added dropwise into the mixture over a period of 30 minutes. At this temperature, reaction was carried out overnight, a saturated aqueous solution of ammonium chloride maintained at 0° C. was added to the reacted mixture, and the mixture was stirred for 10 minutes.

The ether solution was separated, washed with a saturated aqueous solution of sodium chloride, and dried on magnesium sulfate. The solvent was removed by concentration under reduced pressure, and the crude product was purified by the silica gel column chromatography to obtain 0.4 g of (2R,5S)-2,5-diacetyl-1-trityldecanetriol. By carrying out the subsequent treatments in the same manner as described in Example 4, (2R,5S)-2-hydroxy-5-butyl-δ-valerolactone was obtained.

EXAMPLE 1

Preparation of (2R,5R)-2-[4′-(S)-2-methylheptyloxybenzoyloxy]-5-hexyl-δ-valerolactone from (2S,5R)-2-hydroxy-5-hexyl-δ-valerolactone and 4-(S)-2-methylheptyloxybenzoic acid In 40 ml of dehydrated benzene were dispersed 200 mg of (2S,5R)-2-hydroxy-5-hexyl-δ-valerolactone synthesized in Referential Example 4, 250 mg of 4-(S)-2- methylheptyloxybenzoic acid synthesized in Referential Example 5 and 200 μl of azodicarboxylic acid, and 270 mg of triphenylphosphine was added to the dispersion, and the mixture was stirred overnight to effect reaction. Then the reaction mixture was concentrated and was separated and purified by using a silica gel column and n-hexane/benzene as the developing solvent. Recrystallization from ethanol gave 180 mg of (2R,5R)-2-[4'-(S)-2-methylheptyloxybenzoyloxy]-5-hexyl-δ-valerolactone. The phase transition behavior of the obtained compound was determined by using a differential scanning calorimeter and a polarization microscope. The following results were obtained:

$$\text{Cryst.} \underset{22}{\overset{45}{\rightleftarrows}} \text{Iso}$$

In the above results, "Cryst." represents the crystal phase, "Iso" represents the isotropic phase, and the number given in the vicinity of the arrow represents the phase transition temperature (°C.) to the indicated phase.

EXAMPLE 2

Synthesis of (2R,5R)-2-[4-(6-octyloxypyridine-3-carboxy)-benzoyloxy]-5-hexyl-δ-valerolactone In 20 ml of anhydrous benzene were dispersed 200 mg of (2S,5R)-2-hydroxy-5-hexyl-δ-valerolactone and 228 mg of 4-benzyloxybenzoic acid, and 210 μl of diethyl azodicarboxylate and 270 mg of triphenylphosphine were added to the dispersion and the mixture was stirred at room temperature for 16 hours.

The reaction liquid was concentrated and the concentrate was separated and purified by the silica gel column chromatography using n-hexane/benzene as the developing solvent. Recrystallization from an ethanol/hexane mixed solvent gave 240 mg of (2R,5R)-2-(4-benzyloxybenzoyloxy)-5-hexyl-δ-valerolactone. The obtained compound was dissolved in 50 ml of a mixed solvent comprising ethyl acetate and ethanol at a weight ratio of 2/1, 0.1 g of 5% palladium/carbon was added to the solution, and catalytic reduction was carried out under a hydrogen pressure of 1.2 kg/cm² overnight. The catalyst was removed by filtration and the solvent was removed by distillation to obtain 185 mg of (2R,5R)-2-(4-hydroxybenzoyloxy)-5-hexyl-δ-valerolactone.

Separately, 5 g of 6-hydroxypyridine-3-carboxylic acid and 10 g of n-octyl bromide were dissolved in 50 ml of ethanol, 50 ml of a 3N aqueous solution of potassium hydroxide was added to the solution, and the mixture was refluxed for 24 hours. Ethanol was removed from the reacted liquid by distillation, and the residue was neutralized with dilute hydrochloric acid and extracted with ethanol. The excess of n-octyl bromide was separated from the extract by the silica gel column chromatography using n-hexane as the developing solvent. Recrystallization from a mixed solvent of hexane and chloroform gave 5.4 g of 6-octyloxypyridine-3-carboxylic acid.

In 20 ml of methylene chloride were dissolved 138 mg of (2R,5R)-2-(4-hydroxybenzoyloxy)-5-hexyl-δ-valerolactone obtained above and 120 mg of 6-octyloxypyridine-3-carboxylic acid, and 86 mg of dicyclohexylcarbodiimide was added to the solution, and the mixture was stirred at room temperature for 15 hours. The precipitate was removed by filtration, the solvent was removed by concentration, and purification was carried out by the silica gel column chromatography using ethanol and hexane as the developing solvent. Recrystallization from a mixed solvent of ethanol and hexane gave 160 mg of (2R,5R)-2-[4-(6-octyloxypyridine-3-carboxy)-benzoyloxy-5-hexyl-δ-valerolactone.

Figure 3:
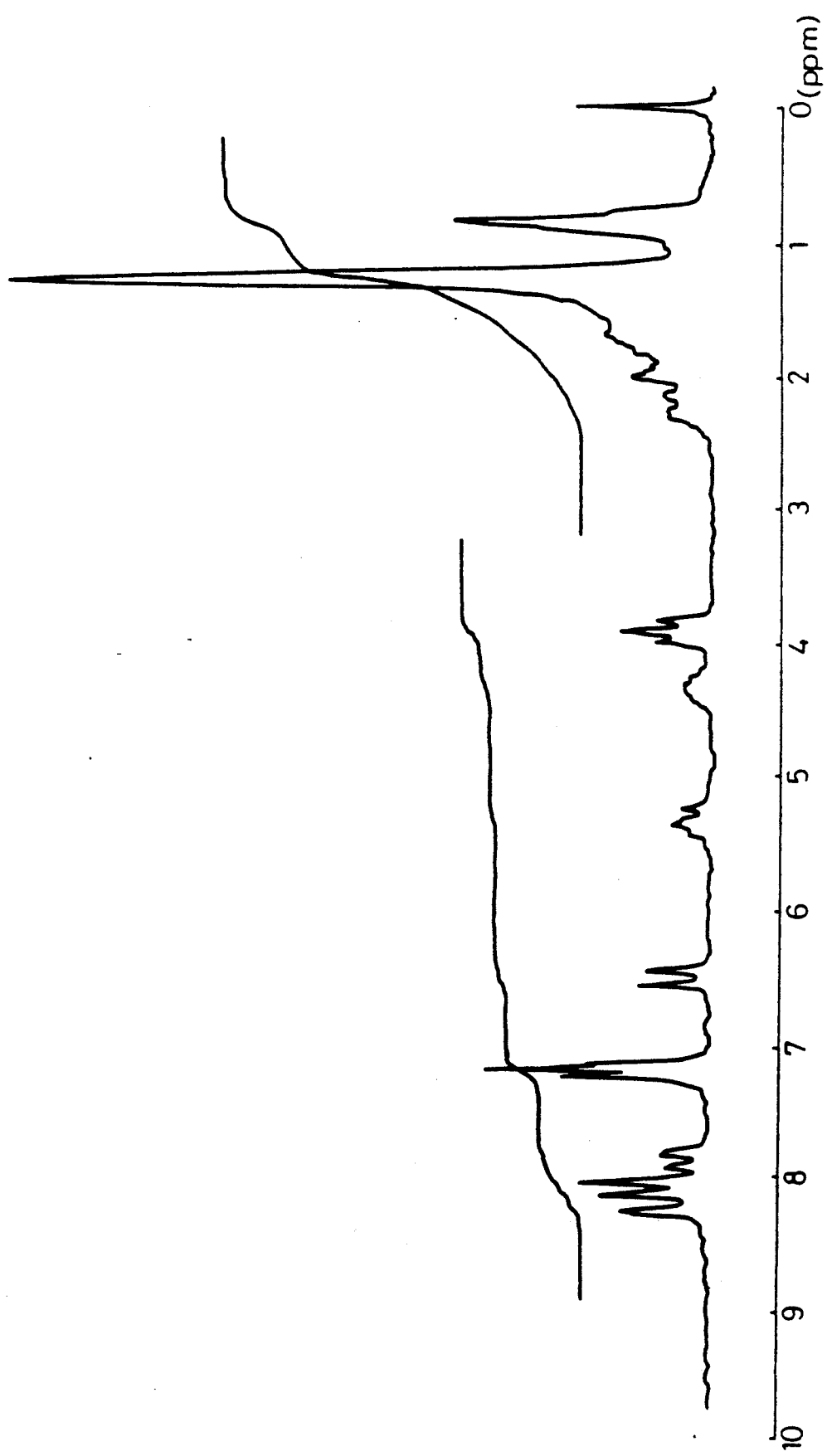
FIG. 3 shows the NMR spectrum of (2R,5S)-2-[4-(6-octyloxypyridine-3-carboxy)-benzoyloxy]-5-hexyl-δ-valerolactone.

The NMR spectrum of the obtained compound is shown in FIG. 3. The compound showed the following phase transition temperatures:

$$\text{Cryst.} \underset{118°\text{C.}}{\overset{129°\text{C.}}{\rightleftarrows}} \text{Iso}$$

EXAMPLES 3 THROUGH 22

Following the same procedure as that described in Example 1, each of the optically active compounds shown in Table I were synthesized from (2S,5R)-2-hydroxy-5-hexyl-δ-valerolactone synthesized in Examples 1, 2 and 3, and each of the carboxylic acids and phenolic derivatives thereof shown in Table I. In Examples 16 and 20, (2S,5R-2-hydroxy-5-butyl-δ-valerolactone and (2S,5R-2-hydroxy-5-methyl-δ-valerolactone were used, respectively, instead of (2S,5R)-2-hydroxy-δ-valerolactone.

The yields and phase transitions of the synthesized optically active compounds are shown in Table I.

TABLE I

| Example No. | Carboxylic acids or phenolic derivatives thereof used as starting substance | Synthesized optically active compounds | Yield (%) | Phase transition (°C.) |
|---|---|---|---|---|
| 3 | 4-(1-methylnonyloxycarbonyl)benzoic acid derivative (C$_8$H$_{17}$*CHCH$_3$-OOC-C$_6$H$_4$-COOH, (S)) | corresponding lactone-phenyl ester with C$_6$H$_{13}$ chain | 60 | Cryst $\longleftrightarrow$ 67 $\longleftrightarrow$ Iso |
| 4 | biphenyl carboxylic acid derivative (C$_8$H$_{17}$*CHCH$_3$-OOC-C$_6$H$_4$-C$_6$H$_4$-COOH, (S)) | corresponding lactone-biphenyl ester with C$_6$H$_{13}$ | 65 | Cryst $\longleftrightarrow$ 97 $\longleftrightarrow$ Iso; Cryst (80) $\longleftrightarrow$ Sx (91) $\longleftrightarrow$ Iso |
| 5 | (C$_{10}$H$_{21}$*CHCH$_3$-OOC-C$_6$H$_4$-OCH$_2$-C$_6$H$_4$-COOH, (S)) | corresponding lactone ester with C$_6$H$_{13}$ | 53 | Cryst $\longleftrightarrow$ 83 $\longleftrightarrow$ Iso |
| 6 | (C$_6$H$_{13}$*CHCH$_3$-O-C$_6$H$_4$-C$_6$H$_4$-COOH, (S)) | corresponding lactone biphenyl ester with C$_6$H$_{13}$ | 62 | Cryst $\longleftrightarrow$ 92 $\longleftrightarrow$ Iso |
| 7 | 1-methyl-1-(4-octylphenyl)methoxy-4-carboxybenzene (C$_8$H$_{17}$-C$_6$H$_4$-*CHCH$_3$-O-C$_6$H$_4$-COOH, (S)) | corresponding lactone ester | 49 | Cryst $\longleftrightarrow$ Iso |
| 8 | HOOC-C$_6$H$_4$-CH$_2$O-C$_6$H$_4$-COOH | corresponding lactone diester with C$_6$H$_{13}$ | 62 | Cryst $\longleftrightarrow$ 154 $\longleftrightarrow$ Iso |
| 9 | (C$_2$H$_5$*CHCH$_3$-CH$_2$O-C$_6$H$_4$-OOC-C$_6$H$_4$-COOH, (S)) | corresponding lactone ester with C$_6$H$_{13}$ | 65 | Cryst $\longleftrightarrow$ 115 $\longleftrightarrow$ Iso |

TABLE I-continued

| Example No. | Carboxylic acids or phenolic derivatives thereof used as starting substance | Synthesized optically active compounds | Yield (%) | Phase transition (°C.) |
|---|---|---|---|---|
| 10 | | | 65 | Cryst ⇌ 116 ⇌ Iso |
| 11 | | | 29 | Cryst ⇌ 103 ⇌ Iso |
| 12 | | | 55 | Cryst ⇌ 83 ⇌ Iso |
| 13 | | | 31 | Cryst ⇌ 95 ⇌ Iso |
| 14 | | | 46 | Cryst ⇌ 110 ⇌ Iso |
| 15 | | | 58 | Cryst ⇌ 103 ⇌ Iso |
| 16 | | | 51 | Cryst ⇌ 112 ⇌ Iso |

TABLE I-continued

| Example No. | Carboxylic acids or phenolic derivatives thereof used as starting substance | Synthesized optically active compounds | Yield (%) | Phase transition (°C.) |
|---|---|---|---|---|
| 17 | (structure) | (structure) | 60 | Cryst ⇌ 98 Iso |
| 18 | (structure) | (structure) | 48 | Cryst ⇌ 90 Iso |
| 19 | (structure) | (structure) | 63 | Cryst ⇌ 108 Iso |
| 20 | (structure) | (structure) | 59 | Cryst ⇌ 90 Iso |
| 21 | (structure) | (structure) | 28 | Cryst ⇌ 108 Iso |
| 22 | (structure) | (structure) | 51 | Cryst ⇌ 85 Iso |

EXAMPLE 23

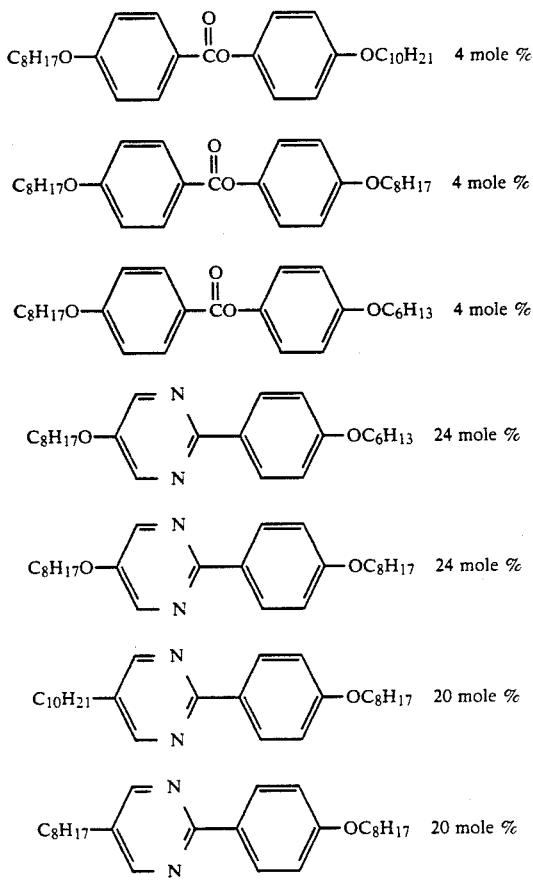

The above-mentioned seven compounds were mixed together to obtain a liquid crystal composition (hereinafter referred to as "composition A1"). The composition A1 showed the following phase transition:

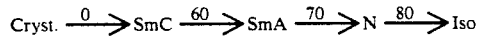

In the above expression, SmC represents the smectic C phase, SmA represents the smectic A phase, and N represents the nematic phase. Since this composition A1 did not contain an optically active compound, the composition was not a ferroelectric liquid crystal and did not show a spontaneous polarization.

A liquid crystal composition (hereinafter referred to as "composition B1") was obtained by mixing 95 mol % of the composition A1 with 5 mole % of the compound obtained in Example 1. This composition B1 showed the chiral smectic phase (Sm*C phase) at temperatures lower than 60° C., and at higher temperatures, the composition B1 showed the SmA phase. At 63° C., the composition B1 showed the N* phase and at 69° C., the composition B1 became an isotropic liquid.

The composition B1 was cast in a cell having a thickness of 2 μm, which was provided with a transparent electrode which had been parallel-oriented by coating a polyimide as the orienting agent on the surface and subjecting the surface to a rubbing treatment, whereby a liquid crystal element was prepared. The liquid crystal element was arranged between two orthogonally crossing polarizers, and an electric field was applied thereto. It was found that the intensity of the transmitted light was changed by application of a voltage of ±20 V. When the response time was determined from this change, it was found that the response time at 25° C. was 180 μsec. It also was found that the tilt angle at 25° C. was 20°.

A liquid crystal composition (hereinafter referred to as "composition B2") was obtained by mixing 80 mole % of the composition A1 with 20 mole % of the compound obtained in Example 1. The composition B2 showed the Sm*C phase at temperatures of from −8° to 53° C., and at higher temperatures, the composition B2 showed the SmA phase. The composition B2 showed the N* phase at 63° C. and became an isotropic liquid. When the response time of the composition B2 was measured in the same manner as described above with respect to the composition B1, it was found that the response time was 200 μsec at 25° C.

A mixture comprising 60 mole % of the composition A1 and 40 mole % of the compound obtained in Example 1 showed the Sm*C phase at temperatures of from −5° to 49° C. and became an isotropic liquid at temperatures higher than 49° C. The response time of this mixture was 180 μsec at 25° C.

Zigzag defects were not substantially found in any of these liquid crystal elements.

EXAMPLE 24

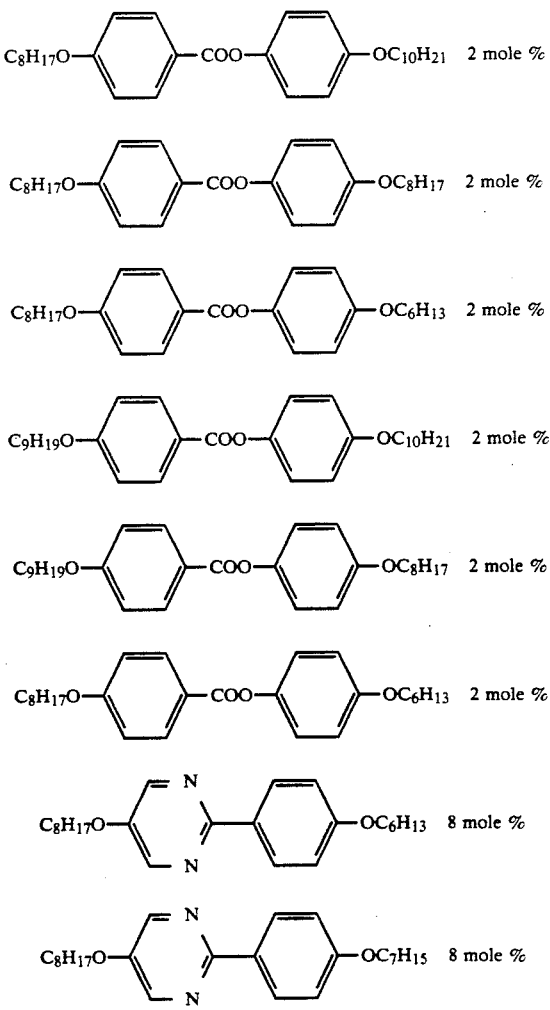

-continued

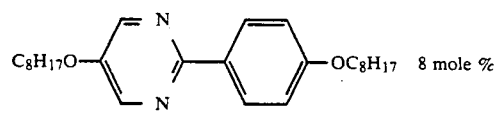 8 mole %

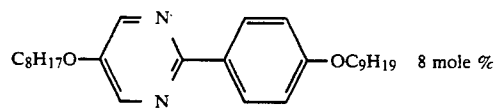 8 mole %

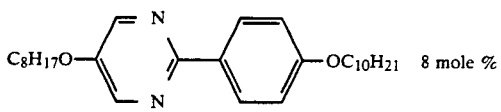 8 mole %

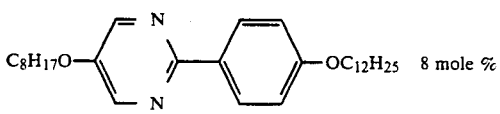 8 mole %

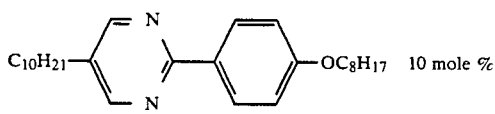 10 mole %

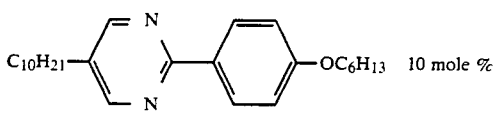 10 mole %

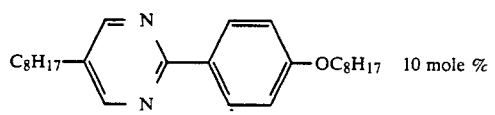 10 mole %

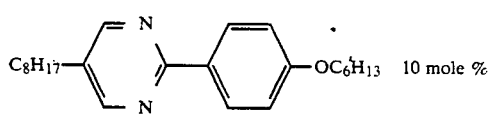 10 mole %

The liquid crystal composition A2 comprising the above-mentioned compounds showed the following phase transition:

Since this liquid crystal composition A2 was composed solely of non-chiral compounds, the liquid crystal composition A2 was not a ferroelectric liquid crystal and did not show a spontaneous polarization.

The composition (hereinafter referred to as "composition B3") obtained by mixing 98 mole % of the above composition A2 with 2 mole % of the compound obtained in Example 2 showed the Sm*C phase at temperatures from room temperature at 57° C., and at higher temperatures the composition B3 showed the SmA phase. The composition B3 showed the N* phase at 71° C. and the composition B3 became an isotropic liquid at 76° C.

The above composition was cast in a cell having a thickness of 2 μm, which was provided with a transparent electrode which had been parallel-oriented by coating a polyimide as the orienting agent on the surface and subjecting the surface to a rubbing treatment, whereby a liquid crystal element was prepared. The liquid crystal element was arranged between two orthogonally crossing polarizers, and an electric field was applied thereto. It was found that the intensity of the transmitted light was changed by application of a voltage of ±20 V. When the response time was determined from this change, it was found that the response time at 50° C. was 46 μsec.

EXAMPLES 25 through 44

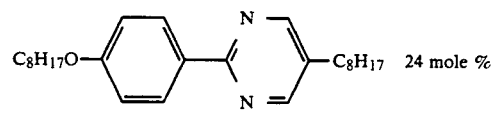 24 mole %

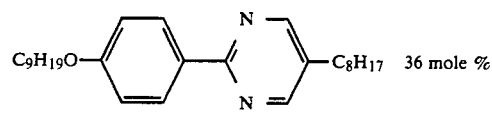 36 mole %

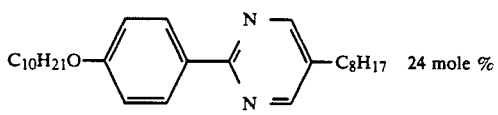 24 mole %

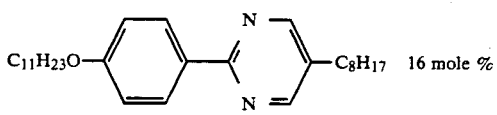 16 mole %

The above-mentioned four compounds were mixed together to obtain a liquid crystal composition (hereinafter referred to as "composition A3"). The composition A3 showed the following phase transition:

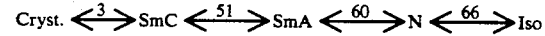

Liquid crystal compositions (hereinafter referred to as "composition B4") were obtained by mixing 98 mole % of the composition A3 with 2 mole % of each of the compounds obtained in Examples 3 through 22. These compositions exhibited the phase transition and response time, which are shown in Table II.

TABLE II

| Example No. | Compounds incorporated with liquid crystal composition A3 | Phase transition (°C) | Response time (μ sec) |
|---|---|---|---|
| 25 | CH₃–C₈H₁₇*CHCO–O–⟨benzene⟩–O–CO–⟨pyranone with C₆H₁₃⟩ | Cryst ←2→ Sm*C ←52→ SmA ←57→ N ←63→ Iso | 810 |
| 26 | CH₃–C₈H₁₇*CHCO–O–⟨biphenyl⟩–⟨pyranone with C₆H₁₃⟩ | Cryst ←2→ Sm*C ←51→ SmA ←58→ N ←66→ Iso | 162 |
| 27 | CH₃–C₁₀H₂₁*CHCO–O–⟨benzene⟩–OCH₂–⟨benzene⟩–O–CO–⟨pyranone with C₆H₁₃⟩ | Cryst ←3→ Sm*C ←51→ SmA ←59→ N ←66→ Iso | 142 |
| 28 | CH₃–C₈H₁₇*CHO–⟨biphenyl⟩–CO–O–⟨pyranone with C₆H₁₃⟩ | Cryst ←2→ Sm*C ←51→ SmA ←59→ N ←65→ Iso | 148 |
| 29 | CH₃–C₈H₁₇*CHO–⟨benzene⟩–CO–O–⟨benzene⟩–CO–O–⟨pyranone with C₆H₁₃⟩ | Cryst ←3→ Sm*C ←49→ SmA ←57→ N ←65→ Iso | — |
| 30 | ⟨pyranone with C₆H₁₃⟩–O–⟨benzene⟩–CH₂O–⟨benzene⟩–CO–O–⟨pyranone with C₆H₁₃⟩ | Cryst ←2→ Sm*C ←52→ SmA ←58→ N ←66→ Iso | — |
| 31 | CH₃–C₂H₅*CHCH₂O–⟨benzene⟩–CO–O–⟨pyranone with C₆H₁₃⟩ | Cryst ←2→ Sm*C ←51→ SmA ←57→ N ←66→ Iso | 230 |

TABLE II-continued

| Example No. | Compounds incorporated with liquid crystal composition A3 | Phase transition (°C.) | Response time (μ sec) |
|---|---|---|---|
| 32 | CH₃<br>C₂H₅*CHCH₂O—⟨phenyl⟩—CH₂O—⟨phenyl⟩—CO—O—[lactone ring with *C, *C, C₆H₁₃] | Cryst ⇌³ Sm*C ⇌⁵² SmA ⇌⁵⁵ N ⇌⁶⁴ Iso | 270 |
| 33 | CH₃<br>C₃H₇*CHOC—⟨phenyl-F⟩—O—⟨phenyl⟩—O—[lactone ring, *C, *C, C₆H₁₃] | Cryst ⇌² Sm*C ⇌⁵¹ SmA ⇌⁵⁷ N ⇌⁶⁶ Iso | — |
| 34 | CH₃<br>C₈H₁₇*CHCO—⟨phenyl⟩—CH₂O—⟨phenyl⟩—CO—O—[lactone ring, *C, *C, C₆H₁₃] | Cryst ⇌³ Sm*C ⇌⁵³ SmA ⇌⁵⁹ N ⇌⁶⁶ Iso | 130 |
| 35 | C₈H₁₇O—⟨pyridyl-N⟩—CO—O—⟨phenyl⟩—O—[tetrahydropyran ring, *C, *C, C₆H₁₃] | Cryst ⇌² Sm*C ⇌⁵¹ SmA ⇌⁵⁶ N ⇌⁶⁵ Iso | 250 |
| 36 | C₈H₁₇O—⟨pyridyl-N⟩—⟨phenyl⟩—O—CO—[lactone ring, *C, *C, C₆H₁₃] | Cryst ⇌³ Sm*C ⇌⁵³ SmA ⇌⁵⁹ N ⇌⁶⁷ Iso | — |
| 37 | C₈H₁₇O—⟨pyridyl-N⟩—CO—O—⟨phenyl⟩—CO—O—[lactone ring, *C, *C, C₆H₁₃] | Cryst ⇌² Sm*C ⇌⁵² SmA ⇌⁵⁸ N ⇌⁶⁶ Iso | 280 |
| 38 | C₁₀H₂₁O—⟨phenyl⟩—CH₂O—⟨pyridyl-N⟩—CO—O—[lactone ring, *C, *C, C₄H₉] | Cryst ⇌¹ Sm*C ⇌⁵¹ SmA ⇌⁵⁷ N ⇌⁶⁸ Iso | 240 |

TABLE II-continued

| Example No. | Compounds incorporated with liquid crystal composition A3 | Phase transition (°C.) | Response time (μ sec) |
|---|---|---|---|
| 39 | C7H15—⟨pyridine⟩—N=N—⟨phenyl⟩—C(=O)O—⟨lactone with C6H13⟩ | Cryst ↔2↔ Sm*C ↔53↔ SmA ↔58↔ N ↔66↔ Iso | 190 |
| 40 | C8H17O—⟨pyridine⟩—CH=N—⟨phenyl⟩—C(=O)O—⟨lactone with C6H13⟩ | Cryst ↔3↔ Sm*C ↔52↔ SmA ↔57↔ N ↔69↔ Iso | — |
| 41 | CH3—C6H13*CHO—⟨fluoro phenyl⟩—C(=O)O—⟨pyridine⟩—C(=O)O—⟨lactone with C6H13⟩ | Cryst ↔2↔ Sm*C ↔52↔ SmA ↔56↔ N ↔67↔ Iso | 200 |
| 42 | CH3—C8H17*CHCH2O—⟨phenyl⟩—C(=O)O—⟨pyridine⟩—C(=O)O—⟨lactone with CH3⟩ | Cryst ↔1↔ Sm*C ↔51↔ SmA ↔57↔ N ↔68↔ Iso | 180 |
| 43 | CH3—C2H5*CHCH2O—⟨phenyl⟩—OCH2—⟨pyridine⟩—O—⟨lactone with C6H13⟩ | Cryst ↔1↔ Sm*C ↔52↔ SmA ↔58↔ N ↔66↔ Iso | 190 |
| 44 | CH3CHCH2*CHCO(Cl)O—⟨phenyl⟩—C(=O)O—⟨pyridine⟩—C(=O)O—⟨lactone with C6H13⟩ | Cryst ↔2↔ Sm*C ↔51↔ SmA ↔59↔ N ↔67↔ Iso | 170 |

We claim:

1. A liquid crystal composition comprising 1 to 90% by mole of at least one optically active compound having a δ-valerolactone ring selected from the group consisting of those represented by the following formulae (1) and (2):

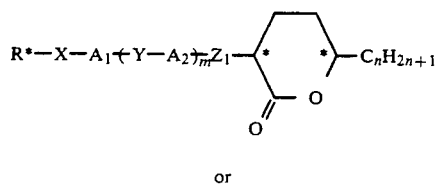
(1)

or

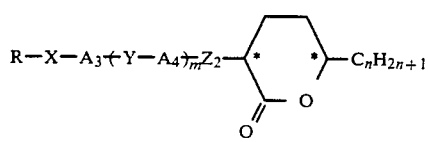
(2)

wherein R* represents $$CH_3(CH_2)_q\text{*}CH(CH_2)_p-$$

with CH₃ branch, in which p is an integer of from 0 to 11 and q is an integer of from 1 to 12, with the proviso that the sum of p and q is up to 12,

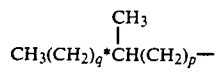

in which l is an integer of from 1 to 14, or

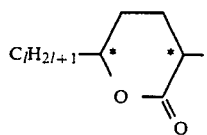

in which k is an integer of from 1 to 14 and $X_1$ is a direct bond or —O—, *C represents an asymmetric carbon atom, R represents a linear alkyl group having 1 to 18 carbon atoms, an optically active monohalogenoalkyl group having 1 to 18 carbon atoms, or an optically active alkyl group having 1 to 18 carbon atoms with a methyl branch, X is a direct bond, —O—, —CO₂—, or —OCO—, with the proviso that when R* is

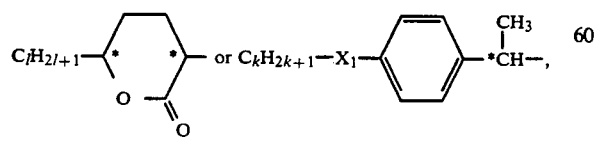

X is —O—, —OCO— or —OCH₂—, Y is a direct bond, —OCO—, —CO₂—, —CH₂O— or —OCH₂—, $A_1$ and $A_2$ represent

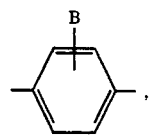

one of $A_3$ and $A_4$ is

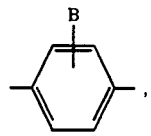

which the other of $A_3$ and $A_4$ represents

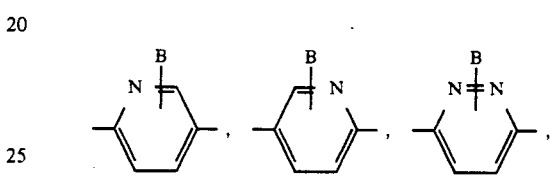

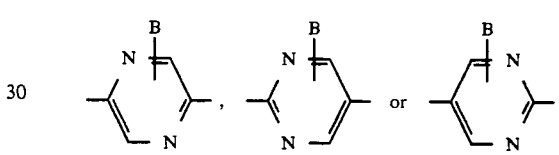

in which B represents a hydrogen atom, a halogen atom such as fluorine or chlorine, or a cyano group, m is 0 or 1, n is an integer of from 1 to 14, $Z_1$ is —CO₂—, —CH₂O— or —O—, and $Z_2$ is —CO₂—, —CH₂O— or —O—, with the proviso that when m is 0 in formula (2), $A_3$ is

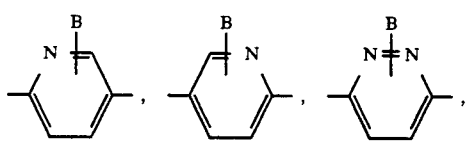

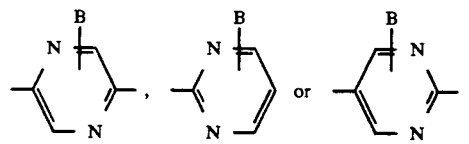

and when Y is a direct bond and $Z_2$ is —O— in formula (2), the combination of $A_3$ and $A_4$ is neither a combination of

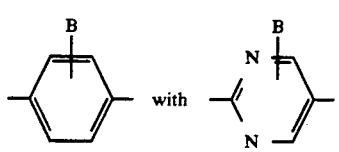

nor a combination of

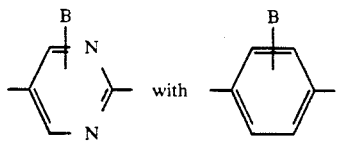 with 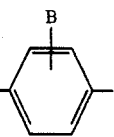

and 10 to 99% by mole of at least one compound selected from the group consisting of ferroelectric liquid crystal compounds and non-ferroelectric liquid crystal compounds exhibiting the smectic C phase.

2. An optically active compound according to claim 1, wherein R in formula (2) is a linear alkyl group having 1 to 14 carbon atoms, an optically active monohalogenoalkyl group having 1 to 14 carbon atoms, or an optically active alkyl group having 1 to 14 carbon atoms with a methyl branch.

3. An optically active compound according to claim 1, wherein R in formula (2) is represented by the formula:

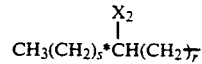

wherein $X_2$ is fluorine, bromine, chlorine or a methyl group, r is an integer of from 0 to 12, and s is an integer of from 0 to 12, with the proviso that the requirement of $2 \leq (r+s) \leq 12$ is satisfied.

* * * * *